(12) United States Patent
Engelhardt et al.

(10) Patent No.: US 9,102,684 B2
(45) Date of Patent: Aug. 11, 2015

(54) INDOLINONE ANALOGUES

(71) Applicants: Harald Engelhardt, Eberichsdorf (AT); Davide Gianni, Vienna (AT); Andreas Mantoulidis, Vienna (AT); Christian Smethurst, Vienna (AT)

(72) Inventors: Harald Engelhardt, Eberichsdorf (AT); Davide Gianni, Vienna (AT); Andreas Mantoulidis, Vienna (AT); Christian Smethurst, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/225,484

(22) Filed: Mar. 26, 2014

(65) Prior Publication Data

US 2014/0296229 A1  Oct. 2, 2014

(30) Foreign Application Priority Data

Mar. 27, 2013  (EP) .................................. 13161486

(51) Int. Cl.
  *C07D 413/04* (2006.01)
  *C07D 413/14* (2006.01)
  *C07D 498/04* (2006.01)

(52) U.S. Cl.
  CPC ............ *C07D 498/04* (2013.01); *C07D 413/04* (2013.01); *C07D 413/14* (2013.01)

(58) Field of Classification Search
  CPC ............................ C07D 413/04; C07D 413/14
  USPC .............................. 548/247; 546/201; 544/137
  See application file for complete search history.

(56) References Cited

FOREIGN PATENT DOCUMENTS

WO    2011054846 A1    5/2011

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Bamborough et al.; Fragment-Based Discovery of Bromodomain Inhibitors Part 2: Optimization of Phenylisoxazole Sulfonamides, J Med. Chem., 2012, vol. 55, No. 2, 587-596.
Duncan et al.; The design and synthesis of 5- and 6-isoxazolylbenzimidazoles as selective inhibitors of the BET bromadomains, Med. Chem. Comm., 2013, vol. 4, No. 1, 140.
International Search Report, form PCT/ISA/210, and Written Opinion, form PCT/ISA/237, for corresponding application PCT/US2014/056079, date of mailing May 15, 2014.

* cited by examiner

*Primary Examiner* — Shawquia Jackson
(74) *Attorney, Agent, or Firm* — Michael P. Morris; Alan R. Stempel

(57) ABSTRACT

The present invention encompasses compounds of general formula (I)

(I)

wherein the groups $R^1$ to $R^4$, $A_1$ and $A_2$ have the meanings given in the claims and in the specification. The compounds of the invention are suitable for the treatment of diseases characterized by excessive or abnormal cell proliferation pharmaceutical preparations containing such compounds and their uses as a medicament.

14 Claims, No Drawings

INDOLINONE ANALOGUES

This invention relates to compounds of the general formula (I)

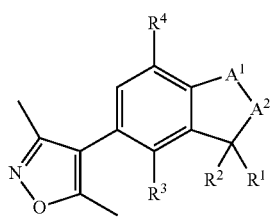

wherein the groups $R^1$ to $R^4$, $A_1$ and $A_2$ have the meanings given in the claims and in the specification. The compounds of the invention are suitable for the treatment of diseases characterized by excessive or abnormal cell proliferation, pharmaceutical preparations containing such compounds and their uses as a medicament. The compounds of the invention are BRD4 inhibitors.

BACKGROUND OF THE INVENTION

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction. Recent research has established a compelling rationale for targeting BRD4 in cancer. BRD4 remains bound to transcriptional start sites of genes expressed during the entry into the G1 phase of the cell cycle, and is functioning to recruit the positive transcription elongation factor complex (P-TEFb), resulting in increased expression of growth promoting genes (Yang and Zhou, Mol. Cell. Biol. 28, 967, 2008) Importantly, BRD4 has been identified as a component of a recurrent t(15; 19) chromosomal translocation in an aggressive form of human squamous carcinoma (French et al., Cancer Res. 63, 304, 2003). Such translocations express the tandem N-terminal bromodomains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the proliferation and the differentiation block of these malignant cells. In addition, BRD4 has been identified as a critical sensitivity determinant in a genetically defined AML mouse model (Zuber et al., Nature 2011 478(7370):524-8). Suppression of BRD4 led to robust anti-leukemic effects in vitro and in vivo, accompanied by terminal myeloid differentiation. Interestingly, BRD4 inhibition triggered MYC down-regulation in a broad array of mouse and human leukemia cell lines examined, indicating that small molecule BRD4 inhibitors may provide a means to suppress the MYC pathway in a range of AML subtypes.

Finally, the other family members of the BET family have also been reported to have some function in controlling or executing aspects of the cell cycle, and have been shown to remain in complex with chromosomes during cell division—suggesting a role in the maintenance of epigenetic memory (Leroy et ai, Mol. Cell. 2008 30(1):51-60).

Examples of bromodomain inhibitors are benzodiazepine derivatives, disclosed in WO2011/054553, and imidazo[4,5] quinoline derivatives, disclosed in WO2011/054846.

Thus, there is the need to provide BRD4 inhibitors useful for the prevention and/or treatment of diseases characterized by excessive or abnormal cell proliferation, such as cancer.

DETAILED DESCRIPTION OF THE INVENTION

The present invention relates to compounds of formula (I)

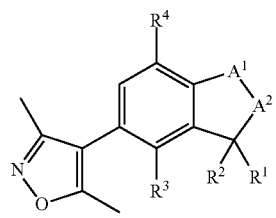

wherein,
$A_1$ is selected from —C=O and —NR$^5$;
$A_2$ is selected from —O—, —C=O and —NR$^6$;
$R^1$ is —H, —OH or —C$_{1-3}$alkyl;
$R^2$ is selected from phenyl, —C$_{5-8}$cycloalkyl, 5-6 membered heteroaryl, 6 to 9 membered heterocycle optionally and independently substituted with one or more $R^7$;
$R^3$ is —H, —C$_{1-3}$alkyl or —O—C$_{1-3}$alkyl;
$R^4$ is —H or —C$_{1-3}$alkyl;
$R^5$ is —H, —C$_{1-3}$alkyl or 6 membered heteroaryl;
$R^6$ is —C$_{1-3}$alkyl, optionally substituted with —N(—C$_{1-3}$ alkyl)$_2$, or $R^6$ is 6 membered heterocycle;
or $R^1$ and $R^6$ taken together form a 5-6 membered heterocycloalkyl;
$R^7$ is selected from halogen, —O—C$_{1-3}$ alkyl, —C$_{1-3}$alkyl, which —C$_{1-3}$alkyl can be optionally substituted with morpholine;
wherein the compounds of formula (I) may be optionally be present in the form of salts.

In a preferred embodiment, the invention relates to compounds of formula (I), wherein $A^1$ is —C=O and $A^2$ is NR$^6$, wherein $R^6$ is —CH$_3$, —CH(CH$_3$)$_2$, —(CH$_2$)$_2$—N(CH$_3$)$_2$, —(CH$_2$)$_3$—N(CH$_3$)$_2$—N-methyl-piperidinyl.

In a preferred embodiment, the invention relates to compounds of formula (I), wherein $A^1$ is NR$^5$ and $A^2$ is —C=O, wherein $R^5$ is —H, —CH$_3$ or pyridyl.

In a preferred embodiment, the invention relates to compounds of formula (I), wherein $A^1$ is NR$^5$ and $A^2$ is —O—.

In a preferred embodiment, the invention relates to compounds of formula (I), wherein $R^1$ is —H, —OH, —CH$_3$.

In a preferred embodiment, the invention relates to compounds of formula (I), wherein $R^2$ is phenyl, optionally substituted with one or more independently selected halogen, —CH$_3$, —O—CH$_3$ and —CH$_2$-morpholine.

In a preferred embodiment, the invention relates to compounds of formula (I), wherein $R^2$ is cyclopentyl, cyclohexyl or spiro[3.5]nonane.

In a preferred embodiment, the invention relates to compounds of formula (I), wherein $R^2$ is thiophenyl or pyridyl, optionally substituted with —$CH_3$ or tetrahydrofuran.

In a preferred embodiment, the invention relates to compounds of formula (I), wherein $R^3$ is —$CH_3$ or —$OCH_3$.

In a preferred embodiment, the invention relates to compounds of formula (I), wherein $R^4$ is —H or —$CH_3$.

In a preferred embodiment, the invention relates to compounds of formula (I), wherein is —H, —$CH_3$ or pyridyl.

In a preferred embodiment, the invention relates to compounds of formula (I), wherein $A^1$ is —C=O and $A^2$ is $NR^6$, $R^6$ and $R^1$ taken together form a oxazolidine or [1,3]oxazine.

In a further embodiment, the invention relates to compounds of formula (I) for use in the treatment of cancer.

In a further embodiment, the invention relates to compound of general formula (I) according to anyone of the embodiments described herein in the description and the claims—or the pharmaceutically acceptable salts thereof—for use in the treatment and/or prevention of cancer.

In a further embodiment, the invention relates to pharmaceutical preparation comprising as active substance one or more compounds of general formula (I) according to anyone of the embodiments described herein in the description and the claims optionally in combination with conventional excipients and/or carriers.

In a further embodiment, the invention relates to pharmaceutical preparation comprising a compound of general formula (I) according to anyone of the embodiments described herein in the description and the claims—or one of the pharmaceutically acceptable salts thereof—and at least one other cytostatic or cytotoxic active substance, different from formula (I).

The present invention further relates to hydrates, solvates, polymorphs, metabolites, derivatives and prodrugs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to compounds of general formula (I)—or the pharmaceutically acceptable salts thereof—for use in the treatment and/or prevention of cancer.

In another aspect the invention relates to the use of the compounds of general formula (I)—or the pharmaceutically acceptable salts thereof—in the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to compounds of general formula (I)—or the pharmaceutically acceptable salts thereof—for use in the treatment and/or prevention of hematopoietic malignancies, preferably AML, MM.

In another aspect the invention relates to compounds of general formula (I)—or the pharmaceutically acceptable salts thereof—for use in the treatment and/or prevention of solid tumors, preferably to lung, liver, colon, brain, thyroid, pancreas, breast, ovary and prostate cancer.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named sub-group is the radical attachment point, for example the substitutent —$C_{1-5}$alkyl-$C_{3-10}$cylcoalkyl, means a $C_{3-10}$cylcoalkyl group which is bound to a $C_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —$NS(O)_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl;

—CH₂CH₂CH₂CH₂CH₃), 2-pentyl (—CH(CH₃)CH₂CH₂CH₃), 3-pentyl (—CH(CH₂CH₃)₂), 3-methyl-1-butyl (iso-pentyl; —CH₂CH₂CH(CH₃)₂), 2-methyl-2-butyl (—C(CH₃)₂CH₂CH₃), 3-methyl-2-butyl (—CH(CH₃)CH (CH₃)₂), 2,2-dimethyl-1-propyl (neo-pentyl; —CH₂ C(CH₃)₃), 2-methyl-1-butyl (—CH₂CH(CH₃)CH₂CH₃).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —CH₃ and —CH₂, —CH₂CH₃ and —CH₂CH₂ or >CHCH₃ etc.

The term "$C_{1-4}$-alkylene" includes for example —(CH₂)—, —(CH₂—CH₂)—, —(CH(CH₃))—, —(CH₂—CH₂—CH₂)—, —(C(CH₃)₂)—, —(CH(CH₂CH₃))—, —(CH(CH₃)—CH₂)—, —(CH₂—CH(CH₃))—, —(CH₂—CH₂—CH₂—CH₂)—, —(CH₂—CH₂—CH(CH₃))—, —(CH(CH₃)—CH₂—CH₂)—, —(CH₂—CH(CH₃)—CH₂)—, —(CH₂—C(CH₃)₂)—, —(C(CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)- and —C(CH₃)(CH₂CH₃)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or H₂N—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or H₂N—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethyl-ethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methyl-ethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

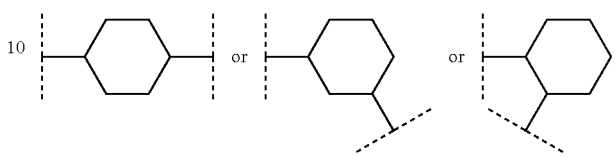

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

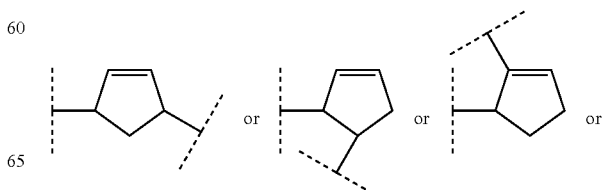

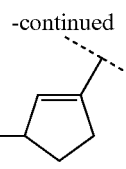

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g. phenyl and

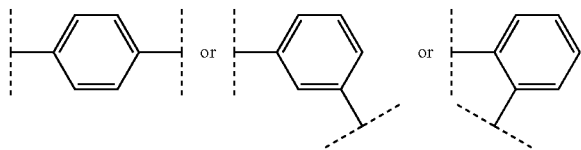

(o, m, p-phenylene), naphthyl and

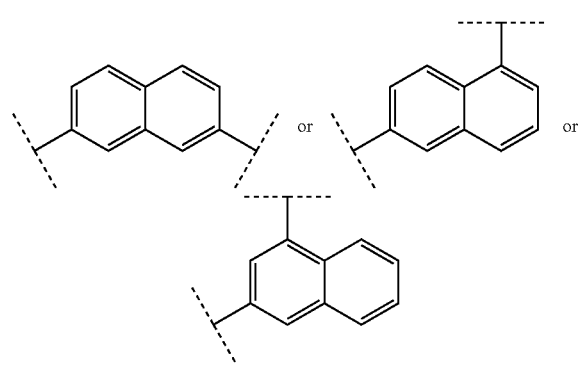

etc.

The above definition for arylene also applies when arylene is part of another group as in HO-aryleneamino or $H_2N$-aryleneoxy for example.

Heterocyclyl or heterocycle denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur sulphoxide→SO, sulphone —$SO_2$—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]-heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]-decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro[4.5]decyl etc.

Further examples are the structures illustrated below, which may be attached via each hydrogen-carrying atom (exchanged for hydrogen):

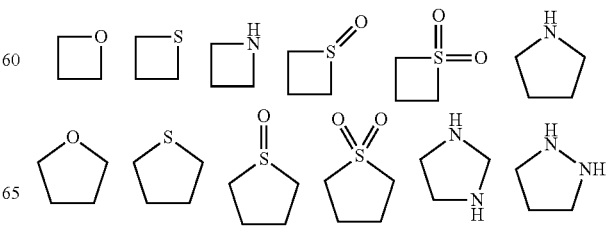

-continued

-continued

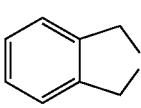 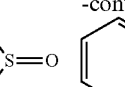 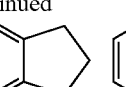
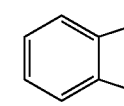 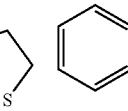 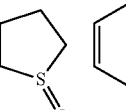
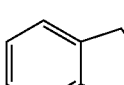 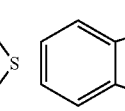 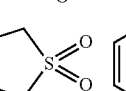
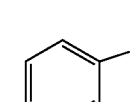 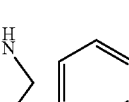 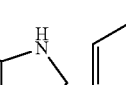
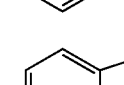 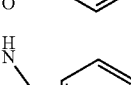 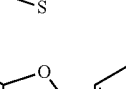
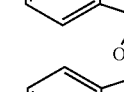 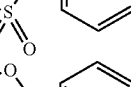 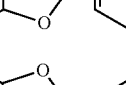
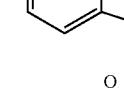 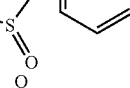 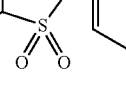
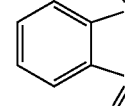 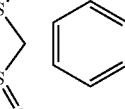 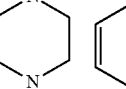
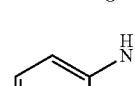 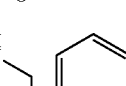 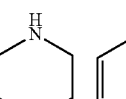
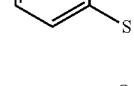 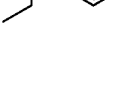 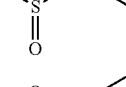

The above definition of heterocyclyl also applies if heterocyclyl is part of another group as in heterocyclylamino or heterocyclyloxy for example.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and

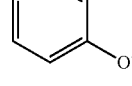 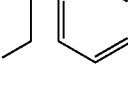 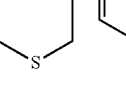

2,3-dihydro-1H-pyrrolyl and

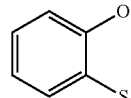 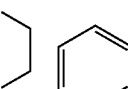 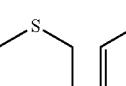

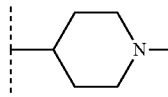

etc.

The above definition of heterocyclylene also applies if heterocyclylene is part of another group as in HO-heterocyclyleneamino or H$_2$N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

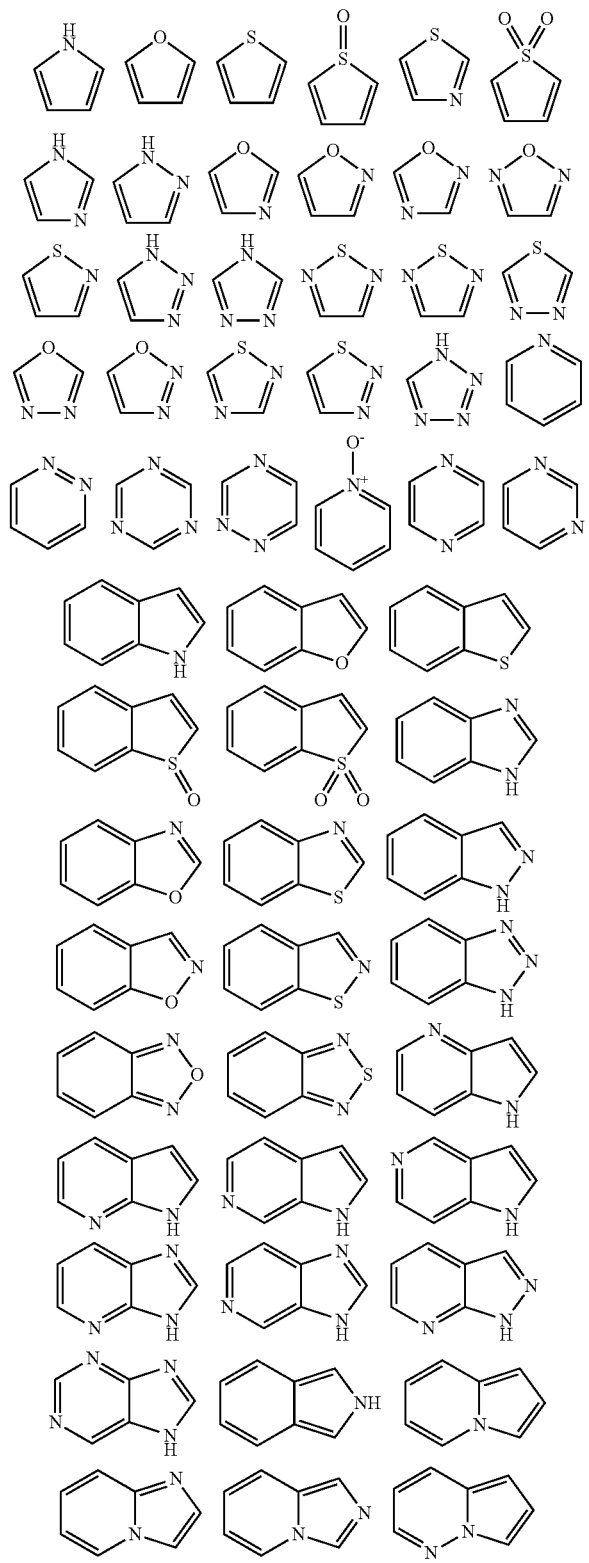

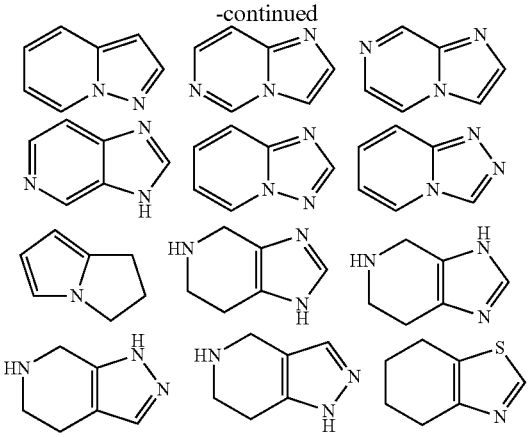

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

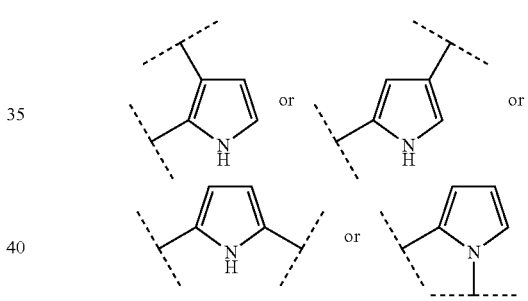

etc.

The above definition of heteroarylene also applies when heteroarylene is part of another group as in HO-heteroaryleneamino or H$_2$N-heteroaryleneoxy, for example.

The bivalent groups mentioned above (alkylene, alkenylene, alkynylene etc.) may also be part of composite groups (e.g. H$_2$N—C$_{1-4}$alkylene- or HO—C$_{1-4}$alkylene-). In this case one of the valencies is saturated by the attached group (here: —NH$_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon to atom that is saturated prior to the substitution. Substitution by a bivalent substituent is therefore only possible at the group —CH$_2$— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

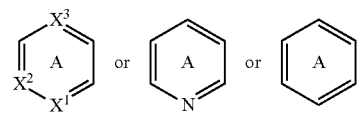

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

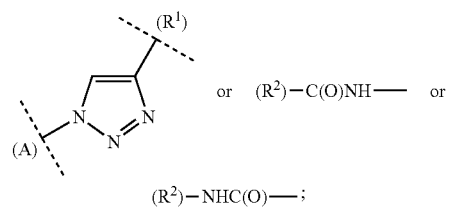

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of Abbreviations

| | |
|---|---|
| ACN, CH$_3$CN | acetonitrile |
| Boc | tert.butoxy carbonyl |
| DCM | dichloromethane |
| DIPEA | diisopropylethyl amine |
| DMAP | dimethyl-pyridin-4-yl-amine |
| DMF | N,N-dimethylformamide |
| DMSO | dimethylsulphoxide |
| EDTA | ethylenediaminetetraacetic acid |
| EtOAc or EA | ethyl acetate |
| FCS | Fetal calf serum |
| h | hour(s) |
| HATU | N-[(dimethylamino)-(1H-1,2,3-triazolo[4,5-b]pyridin-1-yl)-methylene]-N-methylmethanaminium hexafluorophosphate N-oxide |
| HPLC | high performance liquid chromatography |
| KOAc | potassium acetate |
| LiHMDS | lithium hexamethyl disilazide |
| M | Molar |
| Min | minute(s) |
| mL | Milliliter |

-continued

| | |
|---|---|
| MS | mass spectrometry |
| N | Normal |
| NMR | nuclear resonance spectroscopy |
| PE | petrol ether |
| PPh3 | triphenylphosphine |
| DIBAL | diisobutylaluminium hydride |
| RP | reversed phase |
| Rpm | rounds per minute |
| RT or rt | room temperature |
| TBME | tert.butyl methyl ether |
| TEA | triethylamine |
| tert | tertiary |
| TFA | trifluoroacetic acid |
| THF | tetrahydrofuran |
| $t_{Ret}$ | retention time [min] |
| TRIS | tris(hydroxymethyl)aminomethane |
| wt | wild type |
| wt % | weight percent |
| sat. | Saturated |
| nBuLi | n-butyllithium |

Other features and avantages of the present invention will become apparent from the following more detailed Examples which exemplary illustrate the principles of the invention without restricting its scope.

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under to protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18, 5 μm, 30×100 mm Part. No. 186002572; X-Bridge C18, 5 μm, 30×100 mm Part. No. 186002982). The compounds are eluted using either different gradients of H$_2$O/ACN or H$_2$O/MeOH, wherein 0.1% HCOOH is added to the water (acid conditions). For chromatography under basic conditions H$_2$O/ACN gradients are also used, and the water is made basic according to the following recipe: 5 mL of ammonium hydrogen carbonate solution (158 g to 1 L H$_2$O) and 2 mL ammonia (7M in MeOH) are made up to 1 L with H$_2$O.

The normal-phase preparative high pressure chromatography (HPLC) of the example compounds according to the invention is carried out with columns made by Macherey & Nagel (name: Nucleosil, 50-7, 40×250 mm) and VDSoptilab (name: Kromasil 100 NH$_2$, 10 μM, 50×250 mm) The compounds are eluted using different gradients of DCM/MeOH with 0.1% NH$_3$ added to the MeOH.

The analytical HPLC (reaction monitoring) of intermediate compounds is carried out with columns made by Agilent, Waters and Phenomenex. The analytical equipment is also provided with a mass detector in each case.

HPLC Mass Spectroscopy/UV Spectrometry

The retention times/MS-ESI$^+$ for characterising the example compounds according to the invention are produced using an HPLC-MS apparatus (high performance liquid chromatography with mass detector) made by Agilent. Compounds that elute at the injection peak are given the retention time $t_{Ret}$=0.

HPLC-Methods

Preparative prep. HPLC1

| | |
|---|---|
| HPLC: | 333 and 334 Pumps |
| Column: | Waters X-Bridge C18, 5 μm, 30 × 100 mm, Part. No. 186002982 |
| Eluent: | A: 10 mM NH$_4$HCO$_3$ in H$_2$O; B: Acetonitril (HPLC grade) |
| Detection: | UV/Vis-155 |
| Flow: | 50 mL/min |
| Gradient: | 0.00 min: 5% B |
| | 3.00-15.00 min: variable |
| | 15.00-17.00 min: 100% B | prep. HPLC2

| | |
|---|---|
| HPLC: | 333 and 334 Pumps |
| Column: | Waters Sunfire C18, 5 μm, 30 × 100 mm, Part. No. 186002572 |
| Eluent: | A: H$_2$O + 0.2% HCOOH; B: Acetonitril (HPLC grade) + 0.2% HCOOH |
| Detection: | UV/Vis-155 |
| Flow: | 50 mL/min |
| Gradient: | 0.00 min: 5% B |
| | 3.00-15.00 min: variable |
| | 15.00-17.00 min: 100% B |

Analytical Method

AM1

| | |
|---|---|
| HPLC: | Agilent 1100 Series |
| MS: | Agilent LC/MSD SL |
| Column: | Waters, XBridge ™ C18, 2.5 μm, 2.1 × 20 mm Part. No. 186003201 |
| Eluant | A: 0.1% NH$_3$ (=pH 9-10); B: ACN HPLC grade |
| Detection: | MS: Positive and negative |
| Mass range: | 120-800 m/z |
| Flow: | 1.00 mL/min |
| Column temperature: | 60° C. |
| Injection: | 5 μL |
| Gradient: | 0.00 min 5% B |
| | 0.00-2.50 min 5% -> 95% B |
| | 2.50-2.80 min 95% B |
| | 2.81-3.10 min 95% -> 5% B |

AM2

| | |
|---|---|
| HPLC: | Agilent 1200 |
| Column: | Venusil XBP-C18 2.1 × 50 mm, 5 u m+ |
| Eluan: | A: 4 L H$_2$O (with 1.5 ml TFA); B: 4 L Acetonitrile (with 0.75 ml TFA) |
| Flow rate: | 1.0 ml/min |
| Wave length: | 220 nm |
| Column Temp: | 50° C. |

| Gradient: | |
|---|---|
| Time(min) | B % |
| 0.00 | 10 |
| 4.00 | 80 |
| 6.00 | 80 |
| 6.01 | 10 |

AM3

| HPLC: | Agilent 1200 |
| --- | --- |
| Column: | Venusil XBP-C18 2.1 × 50 mm, 5 u m |
| Mobile Phase: | A: 4 L H$_2$O (with 1.5 ml TFA); |
|  | B: 4 L Acetonitrile (with 0.75 ml TFA) |
| Flow rate: | 1.0 ml/min |
| Wave length: | 220 nm |
| Column Temp: | 50° C. |

| Gradient: | |
| --- | --- |
| Time(min) | B % |
| 0.00 | 30 |
| 2.00 | 90 |
| 2.48 | 90 |
| 2.50 | 30 |
| 3.00 | 30 |

AM4

| HPLC: | Agilent 1200 HPLC, 6110MSD |
| --- | --- |
| Column: | Xbridge C18 2.1 × 50 mm, 5 u m |
| Mobile Phase: | A: H$_2$O (10 mmol/L NH$_4$HCO$_3$); |
|  | B: Acetonitrile |
| Flow rate: | 1.0 ml/min |
| Wave length: | 220 nm |
| Column Temp: | 50° C. |

| Gradient: | |
| --- | --- |
| Time(min) | B % |
| 0.00 | 10 |
| 2.00 | 80 |
| 2.48 | 80 |
| 2.50 | 10 |
| 3.00 | 10 |

AM5

| HPLC: | Agilent 1200, 6110MS |
| --- | --- |
| Column: | Venusil XBP-C18 2.1 × 50 mm, 5 u m |
| Mobile Phase: | A: 4 L H$_2$O (with 1.5 ml TFA); |
|  | B: 4 L Acetonitrile (with 0.75 ml TFA) |

| Gradient: | |
| --- | --- |
| Time(min) | B % |
| 0.00 | 10 |
| 0.40 | 10 |
| 3.40 | 100 |
| 3.85 | 100 |
| 3.86 | 10 |

| Flow rate: | 0.8 ml/min |
| --- | --- |
| Wave length: | 220 nm |
| Column Temp: | 50° C |

AM6

| HPLC: | Agilent 1200, 6120MSD |
| --- | --- |
| Column: | Venusil XBP-C18 2.1 × 50 mm, 5 u m |
| Mobile Phase: | A: 4 L H$_2$O (with 1.5 ml TFA); |
|  | B: 4 L Acetonitrile (with 0.75 ml TFA) |
| Flow rate: | 0.8 ml/min |
| Wave length: | 220 nm |
| Column Temp: | 50° C. |

| Gradient: | |
| --- | --- |
| Time(min) | B % |
| 0.00 | 1 |
| 0.40 | 1 |
| 3.40 | 90 |
| 3.85 | 100 |
| 3.86 | 1 |

AM7

| HPLC: | Agilent 1200 |
| --- | --- |
| Column: | Venusil XBP-C18 2.1 × 50 mm, 5 u m |
| Mobile Phase: | A: 4 L H$_2$O (with 1.5 ml TFA); |
|  | B: 4 L Acetonitrile (with 0.75 ml TFA) |
| Flow rate: | 0.8 ml/min |
| Wave length: | 220 nm |
| Column Temp: | 50° C. |

| Gradient: | |
| --- | --- |
| Time(min) | B % |
| 0.00 | 25 |
| 0.40 | 25 |
| 3.40 | 100 |
| 3.85 | 100 |
| 3.86 | 25 |
| 4.50 | 25 |

AM8

| HPLC: | Agilent 1100/1200 Series |
| --- | --- |
| MS: | Agilent 1100 LC/MSD SL |
| Column: | Waters Sunfire, 5.0 μm, 2.1 × 50 mm |
| Eluent: | A: H$_2$O + 0.2% HCOOH; B: CH$_3$CN |
| Detection:: | ESI |
| Mass range: | 100-1200 m/z |
| Flow: | 1.20 mL/min |
| Column temp: | 35° C. |

| Gradient: | 0.01 min: | 5% B |
| --- | --- | --- |
|  | 0.01-1.50 min: | 5% → 95% B |
|  | 1.50-2.00 min: | 100% B |

AM9
HPLC: Agilent 1100/1200 Series
MS: Agilent 1100 LC/MSD SL
Column: WatersXBridge C18 2.1×50 mm, 5.0μ
Gradient: 95:5 Water (5 mM NH$_4$HCO$_3$, 19 mM NH$_3$):
 CH$_3$CN in 1.24 min from 5:95, 0.75 min isocratic to 5:95
Flow: 1.2 mL/min
AM10

| HPLC: | Agilent 1100 Series |
| --- | --- |
| MS: | Agilent LC/MSD G6140 A |
| Column: | Agilent Poroshell SB C18, 2.7 μm, 2.1 × 30 mm |
| Eluent: | A: 0.11% formic acid in H$_2$O; |
|  | B: 0.1% formic acid in CH$_3$CN |
| Detection: | MS: Positive mode |
| Mass range: | 150-700 m/z |
| Flow: | 1.40 mL/min |
| Column temp: | 45° C. |

| Gradient: | 0.00 min: | 15% B |
| --- | --- | --- |
|  | 0.00-1.00 min: | 15% → 95% B |
|  | 1.00-1.13 min: | 95% B |
| Stop time: | 1.23 min | |

AM11

| HPLC: | Agilent 1100/1200 Series |
|---|---|
| MS: | Agilent LC/MSD SL |
| Column: | Waters X-Bridge C18 OBD, 5 μm, 2.1 × 50 mm |
| Eluent: | A: 5 mM $NH_4HCO_3$/19 mM $NH_3$ in $H_2O$; |
| | B: $CH_3CN$ |
| Detection: | MS: Multimode ESI Positive and negative mode |
| Mass range: | 105-1200 m/z |
| Flow: | 1.20 ml/min |
| Column temp: | 35° C. |
| Gradient: | 0.00-1.25 min: 5% → 100% B |
| | 1.25-2.00 min: 100% B |
| | 2.00-2.01 min: 100% → 5% B |

AM12

| HPLC: | Agilent 1200 |
|---|---|
| MS: | Agilent LC/MSD SL |
| Column: | Venusil XBP-C18 2.1 × 50 mm, 5 μm |
| Eluent: | A: 4 L $H_2O$ (with 1.5 ml TFA); |
| | B: 4 L $CH_3CN$ (with 0.75 ml TFA) |
| Flow rate: | 1.0 ml/min |
| Column temp: | 50° C. |
| Gradient: | 0.00 min 10% B |
| | 2.00 min 80% B |
| | 2.48 min 80% B |
| | 2.50 min 10% B |
| | 3.00 min 10% B |

Example 1

Preparation of 5-(3,5-Dimethyl-isoxazol-4-yl)-3-(3-fluoro-5-methoxy-phenyl)-2-methyl-2,3-dihydro-isoindol-1-one

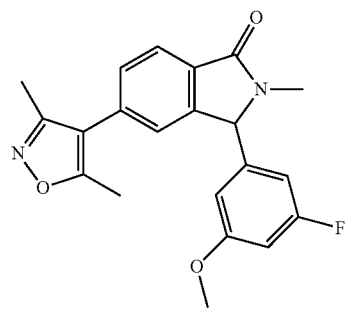

Reaction scheme:

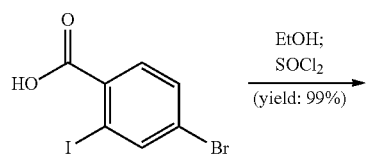

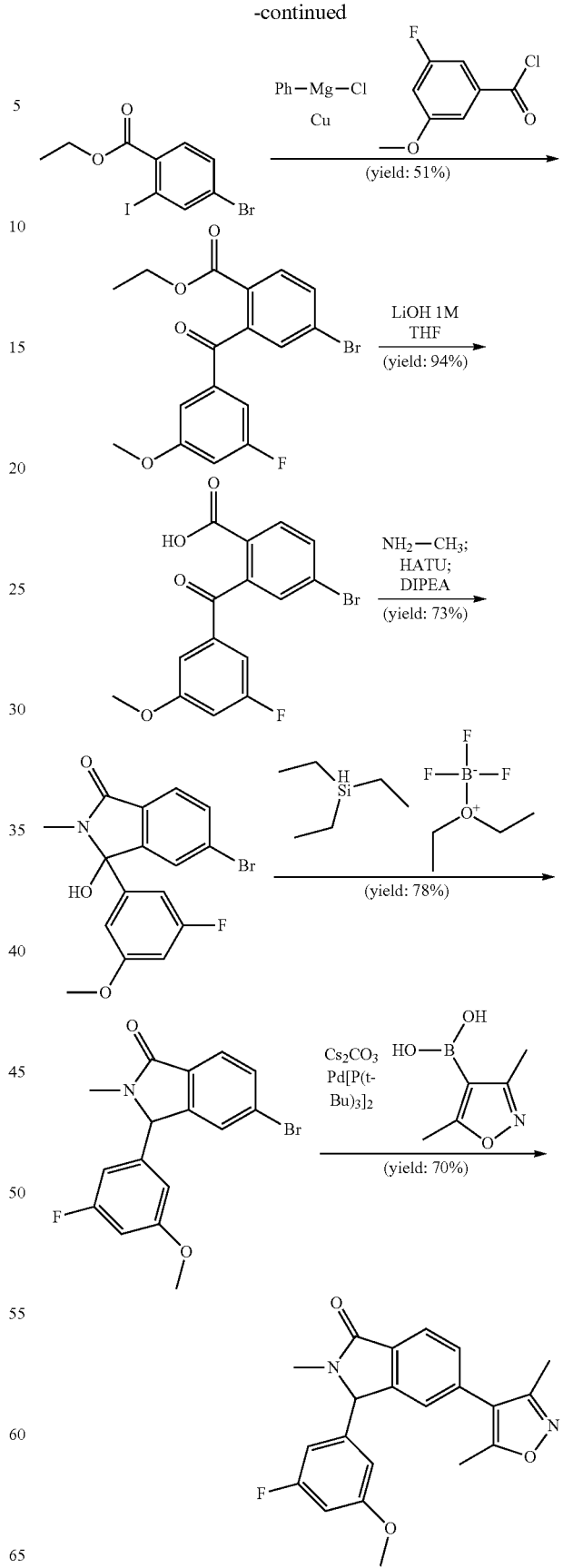

4-Bromo-2-iodo-benzoic acid ethyl ester

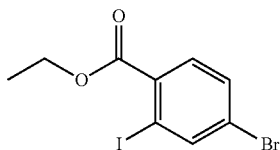

4-Bromo-2-iodo-benzoic acid (4.0 g; 12.24 mmol) is stirred in thionyl chloride (8.0 ml) under reflux for 1 hour. The reaction mixture is evaporated under reduced pressure and taken up immediately in 20 ml methylene dichloride and cooled down to 0° C. Ethanol (20.0 ml; 342.96 mmol) is added and stirred for 1 hour at ambient temperature. The ethanol is evaporated and the residue taken up in methylene dichloride and extracted with saturated NaHCO$_3$ solution. The organic layer is separated, dried over MgSO$_4$ and evaporated to dryness.

Yield: 99% (4.28 g; 12.06 mmol)

HPLC-MS: (M+H)$^+$=355/357; t$_{Ret}$=2.12 min; AM11

4-Bromo-2-(3-fluoro-5-methoxy-benzoyl)-benzoic acid ethyl ester

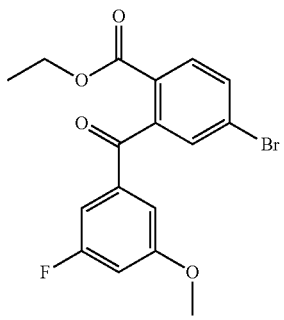 [SMILES: CCOC(=O)c1ccc(Br)cc1C(=O)c1cc(F)cc(OC)c1]

In a dried and argon flushed reaction vessel is weight in 4-Bromo-2-iodo-benzoic acid ethyl ester (300 mg; 0.85 mmol). It is solved in 2.0 ml dried tetrahydrofuran and cooled down to −40° C. Then, phenylmagnesium chloride 2.0 mol/l (465 µl; 0.93 mmol) is dropped to the solution. After the metal halogen exchange is completed copper (I) cyanide di(lithium chloride)complex 1.0 mol/l (845 µl; 0.85 mmol) is added and stirred for 15 minutes at −40° C. 3-fluoro-5-methoxy-benzoyl chloride (191.26 mg; 1.01 mmol) is added and stirred for 30 minutes at −40° C. and 30 minutes at ambient temperature. The reaction mixture is quenched with 1 ml saturated NH$_4$Cl solution and poured into water. The water phase is extracted two times with ethyl acetate, the combined organic phases washed once with brine and water, then dried and evaporated to dryness. The residue is taken up in methylene dichloride and purified via reversed phase chromatography under basic conditions.

Yield: 51% (165 mg; 0.43 mmol)

HPLC-MS: (M+H)$^+$=381/383; t$_{Ret}$=1.99 min; AM9

4-Bromo-2-(3-fluoro-5-methoxy-benzoyl)-benzoic acid

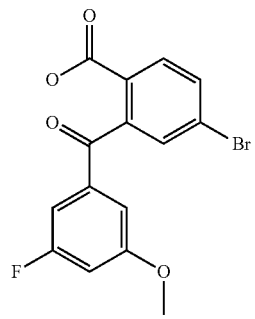 [SMILES: COc1cc(F)cc(C(=O)c2cc(Br)ccc2C(=O)O)c1]

To a solution of 4-Bromo-2-(3-fluoro-5-methoxy-benzoyl)-benzoic acid ethyl ester (165 mg; 0.43 mmol) in 900 µl tetrahydrofuran is added a 1 M solution of LiOH in water (866 µl; 0.87 mmol). It is stirred at ambient temperature for 2 hours. The reaction mixture is acidified with 1 N HCl and washed with methylene dichloride several times. The organic layers are pooled, dried over MgSO$_4$ and evaporated to dryness.

Yield: 94% (144 mg; 0.41 mmol)

HPLC-MS: (M+H)$^+$=353/355; t$_{Ret}$=1.47 min; AM9

5-Bromo-3-(3-fluoro-5-methoxy-phenyl)-3-hydroxy-2-methyl-2,3-dihydro-isoindol-1-one

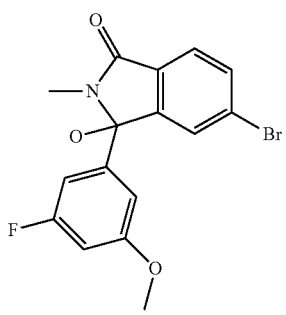 [SMILES: COc1cc(F)cc(C2(O)c3cc(Br)ccc3C(=O)N2C)c1]

4-Bromo-2-(3-fluoro-5-methoxy-benzoyl)-benzoic acid (140 mg; 0.39 mmol) is dissolved in 1.4 ml N,N-dimethylformamide, treated with N,N-Diisopropylethylamine (154 µl; 1.19 mmol) and HATU (66 mg; 0.44 mmol). It is stirred at ambient temperature for 5 minutes before 2.0 mol/l methylamine (341 µl; 0.80 mmol) is added. After 16 hours the reaction mixture is purified via reversed phase chromatography under basic conditions.

Yield: 73% (106 mg; 0.29 mmol)

HPLC-MS: (M+H)$^+$=366/368; t$_{Ret}$=1.76 min; AM9

27

5-Bromo-3-(3-fluoro-5-methoxy-phenyl)-2-methyl-2,3-dihydro-isoindol-1-one

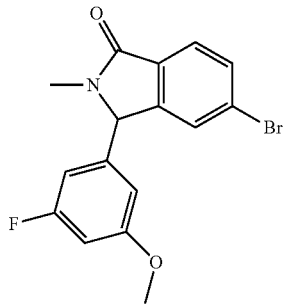 [SMILES: COc1cc(F)cc(C2c3cc(Br)ccc3C(=O)N2C)c1]

To a well stirred suspension of 5-Bromo-3-(3-fluoro-5-methoxy-phenyl)-3-hydroxy-2-methyl-2,3-dihydro-isoindol-1-one (106 mg; 0.29 mmol) in ethylene dichloride (1 ml) at 0° C. is added Triethylsilane (84 mg; 0.72 mmol) and Boron Trifluorid etherate (54 µl; 0.43 mmol). It is let to come to ambient temperature and stirred for 1 hour. The reaction mixture is then purified by using reversed phase chromatography under basic conditions.

Yield: 78% (79 mg; 0.23 mmol)

HPLC-MS: $(M+H)^+$=350/352; $t_{Ret}$=1.81 min; AM9

28

5-(3,5-Dimethyl-isoxazol-4-yl)-3-(3-fluoro-5-methoxy-phenyl)-2-methyl-2,3-dihydro-isoindol-1-one

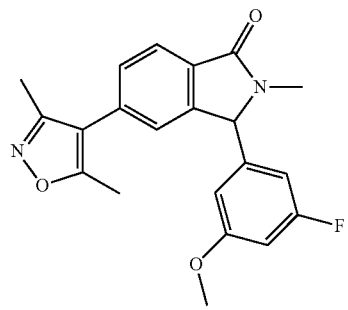

5-Bromo-3-(3-fluoro-5-methoxy-phenyl)-2-methyl-2,3-dihydro-isoindol-1-one (79 mg; 0.23 mmol); 3,5-Dimethyl-4-isoxazolylboronic acid (79 mg; 0.56 mmol); 70% Cesiumcarbonate (110 n1; 0.54 mmol) and Bis(tri-t-butylphosphine)palladium(0) (23 mg; 0.05 mmol) are slurred up in tetrahydrofurane (800 n1) and stirred for 3 hours at 50° C.

The reaction mixture is then purified by using reversed phase chromatography under basic conditions.

Yield: 70% (58 mg; 0.16 mmol)

HPLC-MS: $(M+H)^+$=367; $t_{Ret}$=1.18 min; AM1

The following compounds are prepared using a similar procedure as described for 5-(3,5-Dimethyl-isoxazol-4-yl)-3-(3-fluoro-5-methoxy-phenyl)-2-methyl-2,3-dihydro-isoindol-1-one:

| EX # | Structure | Name | Yield [%] | HPLC-MS (AM1): |
|---|---|---|---|---|
| 2 | 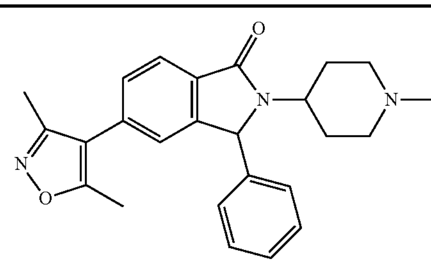 | 5-(3,5-Dimethyl-isoxazol-4-yl)-2-(1-methyl-piperidin-4-yl)-3-phenyl-2,3-dihydro-isoindol-1-one | 62 | M + H⁺ = 402<br>$t_{Ret}$ = 1.13 min |
| 3 | 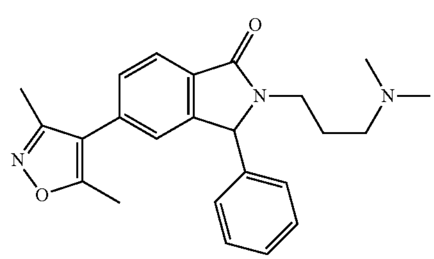 | 2-(3-Dimethylamino-propyl)-5-(3,5-dimethyl-isoxazol-4-yl)-3-phenyl-2,3-dihydro-isoindol-1-one | 55 | M + H⁺ = 390<br>$t_{Ret}$ = 1.13 min |
| 4 | 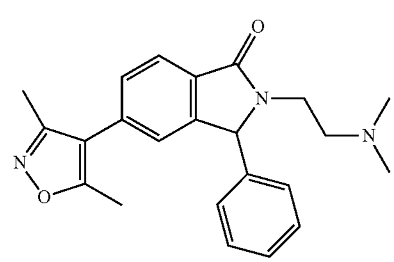 | 2-(2-Dimethylamino-ethyl)-5-(3,5-dimethyl-isoxazol-4-yl)-3-phenyl-2,3-dihydro-isoindol-1-one | 60 | M + H⁺ = 376<br>$t_{Ret}$ = 1.16 min |

| EX # | Structure | Name | Yield [%] | HPLC-MS (AM1): |
|---|---|---|---|---|
| 5 | 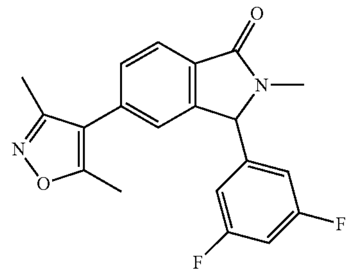 | 3-(3,5-Difluoro-phenyl)-5-(3,5-dimethyl-isoxazol-4-yl)-2-methyl-2,3-dihydro-isoindol-1-one | 55 | M + H⁺ = 355 $t_{Ret}$ = 1.19 min |
| 6 | 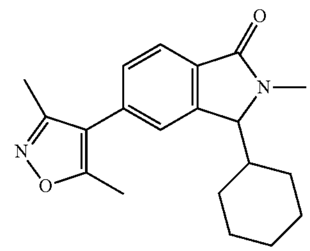 | 3-Cyclohexyl-5-(3,5-dimethyl-isoxazol-4-yl)-2-methyl-2,3-dihydro-isoindol-1-one | 62 | M + H⁺ = 325 $t_{Ret}$ = 1.24 min |
| 7 | 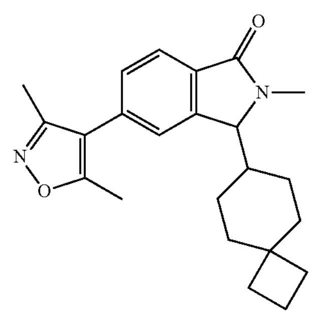 | 5-(3,5-Dimethyl-isoxazol-4-yl)-2-methyl-3-spiro[3.5]non-7-yl-2,3-dihydro-isoindol-1-one | 61 | M + H⁺ = 365 $t_{Ret}$ = 1.41 min |

Example 8

Preparation of 5-(3,5-Dimethyl-isoxazol-4-yl)-2-methyl-3-phenyl-2,3-dihydro-isoindol-1-one

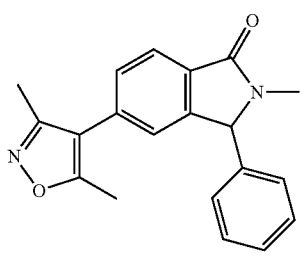

Reaction scheme:

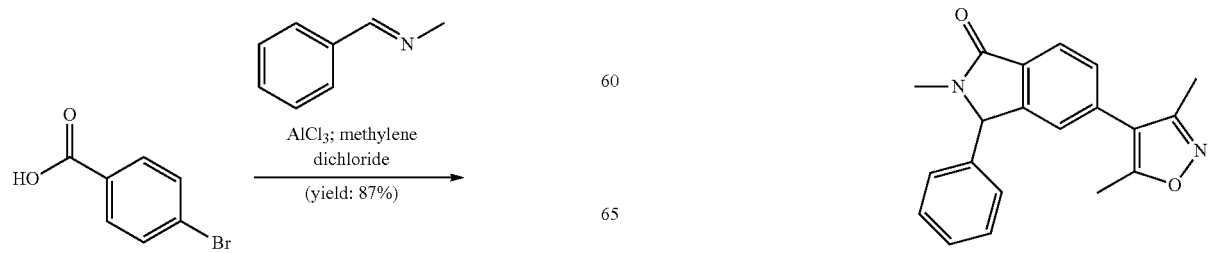

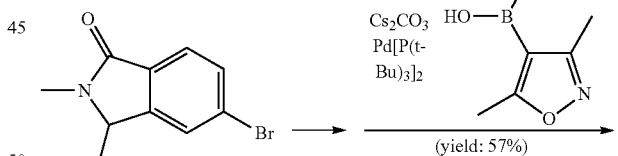

5-Bromo-2-methyl-3-phenyl-2,3-dihydro-isoindol-1-one

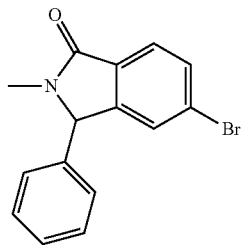 [SMILES: CN1C(=O)c2ccc(Br)cc2C1c1ccccc1]

To a solution of N-Benzylidenemethylamine (3.8 g; 31.9 mmol) in methylene dichloride (100 ml) is added a solution of 4-Bromobenzoylchloride (7.0 g; 31.9 mmol) in methylene dichloride (50 ml) drop wise. The mixture is stirred at ambient to temperature for 16 hours. AlCl$_3$ (4.3 g; 32.58 mmol) is added to the above mixture at 0° C. The mixture is stirred at ambient temperature for 16 hours. Another portion of AlCl$_3$ (4.3 g; 32.58 mmol) is added to the above mixture at 0° C. and the mixture is stirred at ambient temperature overnight. The mixture is poured into ice and extracted with methylene dichloride. The combined organic phase is washed with water and brine, dried over Na$_2$SO$_4$, filtered and concentrated. The residue is purified by silica chromatography.

Yield: 87% (8.3 g; 27.47 mmol)

HPLC-MS: (M+H)$^+$=302/304; $t_{Ret}$=1.79 min; AM9

5-(3,5-Dimethyl-isoxazol-4-yl)-2-methyl-3-phenyl-2,3-dihydro-isoindol-1-one

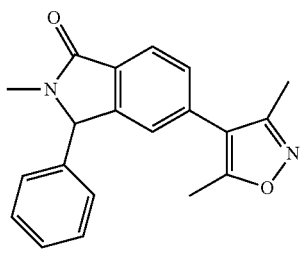 [SMILES: Cc1noc(C)c1-c1ccc2c(c1)C(c1ccccc1)N(C)C2=O]

5-Bromo-2-methyl-3-phenyl-2,3-dihydro-isoindol-1-one (20 mg; 0.07 mmol); 3,5-Dimethyl-4-isoxazolylboronic acid (16 mg; 0.12 mmol); 70% Cesiumcarbonate (32 µl; 0.16 mmol) and Bis(tri-t-butylphosphine)palladium(0) (7 mg; 0.02 mmol) are slurred up in tetrahydrofuran (200 µl) and stirred for 2 hours at 50° C.

The reaction mixture is then purified by using reversed phase chromatography under basic conditions.

Yield: 57% (12 mg; 0.04 mmol)

HPLC-MS: (M+H)$^+$=319; $t_{Ret}$=1.11 min; AM1

Example 9

Preparation of (S)-5-(3,5-Dimethyl-isoxazol-4-yl)-2-methyl-3-phenyl-2,3-dihydro-isoindol-1-one

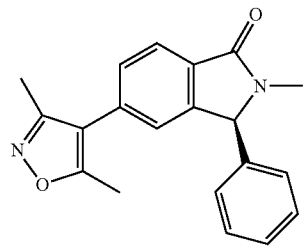

Chiral separation of 5-(3,5-Dimethyl-isoxazol-4-yl)-2-methyl-3-phenyl-2,3-dihydro-isoindol-1-one leads to the (S) and (R) enantiomers.

HPLC: Thar preparative SFC 80

Column: Chiralpak AS-H, 250×30 mm I D

Mobile phase: A for CO$_2$ and B for MeOH (0.05% IPAm)

Gradient: A:B=60:40

Flow rate: 65 ml/min

Back pressure: 100 bar

Column temperature: 40° C.

Wavelength: 220 nm

Example 10

Preparation of 5-(3,5-Dimethyl-isoxazol-4-yl)-2,3-dimethyl-3-phenyl-2,3-dihydro-isoindol-1-one

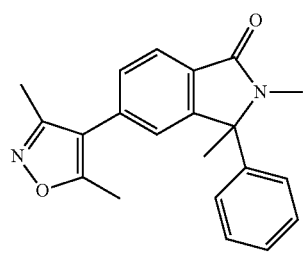

Reaction scheme:

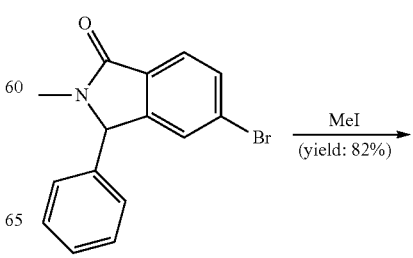

-continued

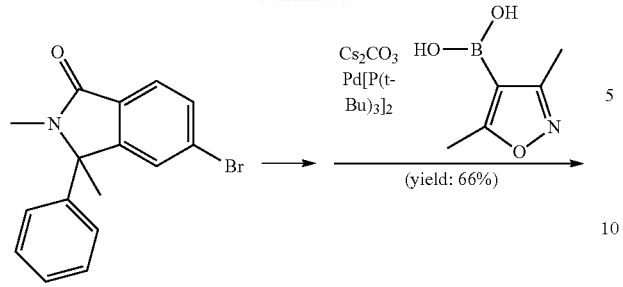
(yield: 66%)

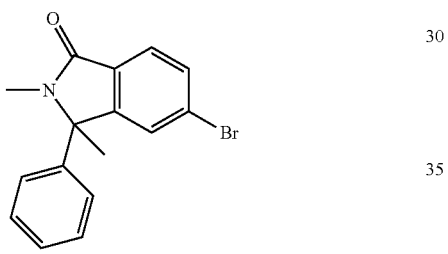

5-Bromo-2,3-dimethyl-3-phenyl-2,3-dihydro-isoindol-1-one

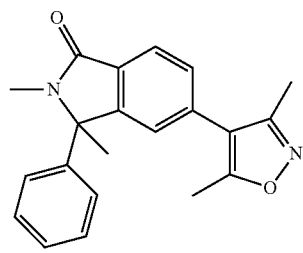 [SMILES: Cc1noc(C)c1-c1ccc2c(c1)C(C)(c1ccccc1)N(C)C2=O]

To a solution of 5-Bromo-2-methyl-3-phenyl-2,3-dihydro-isoindol-1-one (250 mg; 0.83 mmol) in 2.5 ml of anhydrous tetrahydrofuran at –30° C. is added an 0.5 mol/l potassium bis(trimethylsilyl)amide (2.5 ml; 1.24 mmol) solution. After 30 minutes iodomethane (77 µl; 1.24 mmol) is added and stirred for 16 hours at –30° C. The reaction mixture is diluted with methanol and purified via reversed phase chromatography under basic conditions.

Yield: 82% (215 mg; 0.68 mmol)
HPLC-MS: $(M+H)^+$=316/318; $t_{Ret}$=1.24 min; AM1

5-(3,5-Dimethyl-isoxazol-4-yl)-2,3-dimethyl-3-phenyl-2,3-dihydro-isoindol-1-one

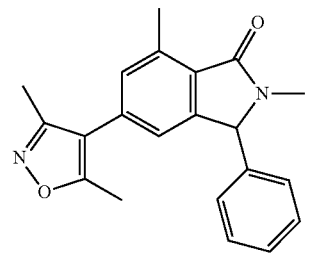

Analogue to the procedure described for 5-(3,5-Dimethyl-isoxazol-4-yl)-2-methyl-3-phenyl-2,3-dihydro-isoindol-1-one.

Yield: 66% (149 mg; 0.45 mmol)
HPLC-MS: $(M+H)^+$=333; $t_{Ret}$=1.14 min; AM1

Example 11

Preparation of 5-(3,5-Dimethyl-isoxazol-4-yl)-2,7-dimethyl-3-phenyl-2,3-dihydro-isoindol-1-one

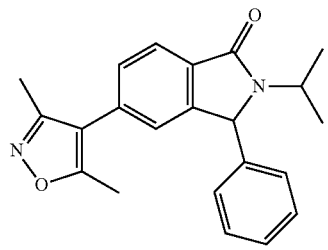 [SMILES: Cc1noc(C)c1-c1ccc2c(c1)C(c1ccccc1)N(C(C)C)C2=O]

Analogue to the procedure described for 5-(3,5-Dimethyl-isoxazol-4-yl)-2-methyl-3-phenyl-2,3-dihydro-isoindol-1-one.

Yield: 74% (58 mg; 0.17 mmol)
HPLC-MS: $(M+H)^+$=333; $t_{Ret}$=1.22 min; AM1

Example 12

Preparation of 5-(3,5-Dimethyl-isoxazol-4-yl)-2-isopropyl-3-phenyl-2,3-dihydro-isoindol-1-one Reaction scheme:

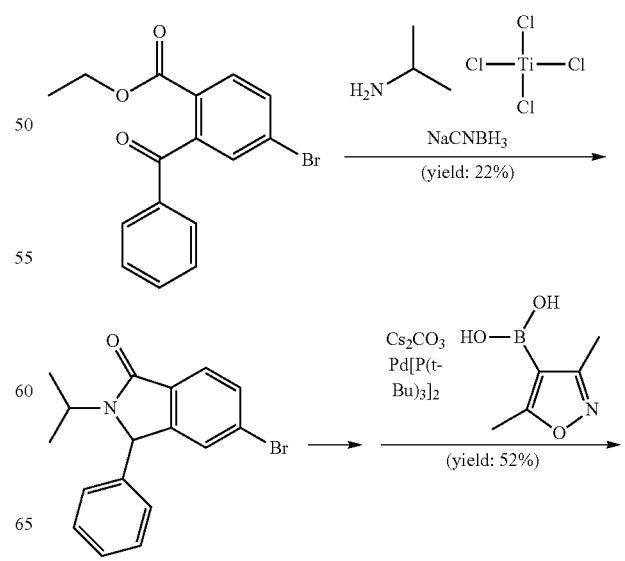

-continued

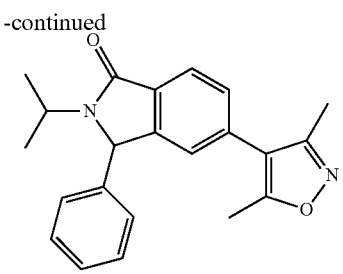

5-Bromo-2-isopropyl-3-phenyl-2,3-dihydro-isoindol-1-one

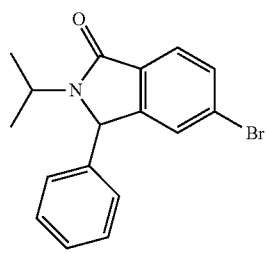 [SMILES: CC(C)N1C(=O)c2ccc(Br)cc2C1c1ccccc1]

2-Benzoyl-4-bromo-benzoic acid ethyl ester (50 mg; 0.15 mmol) is dissolved in ethylene dichloride (1 ml) and treated with 1 mol/l Titanium(IV)chloride solution (150 µl; 0.15 mmol) and cooled down to 0° C. Isopropylamine (13 µl; 0.15 mmol) is added and stirred for 2 hours at ambient temperature and 16 hours at 80° C. A 6.5 mol/l solution of sodium cyano borohydride in methanol (140 µl; 0.90 mmol) is added and stirred for 3 days followed by another portion of sodium cyano borohydride in methanol and 16 hours at 50° C.

Product collection by using reversed phase chromatography under acid conditions.

Yield: 22% (11 mg; 0.03 mmol)

HPLC-MS: (M+H)$^+$=330/332; $t_{Ret}$=1.89 min; AM9

5-(3,5-Dimethyl-isoxazol-4-yl)-2-isopropyl-3-phenyl-2,3-dihydro-isoindol-1-one

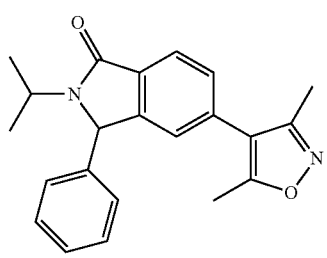 [SMILES: Cc1noc(C)c1-c1ccc2c(c1)C(c1ccccc1)N(C(C)C)C2=O]

Analogue to the procedure described for 5-(3,5-Dimethyl-isoxazol-4-yl)-2-methyl-3-phenyl-2,3-dihydro-isoindol-1-one.

Yield: 52% (6 mg; 0.02 mmol)

HPLC-MS: (M+H)$^+$=347; $t_{Ret}$=1.27 min; AM1

Example 13

Preparation of 5-(3,5-Dimethyl-isoxazol-4-yl)-3-phenyl-3H-isobenzofuran-1-one

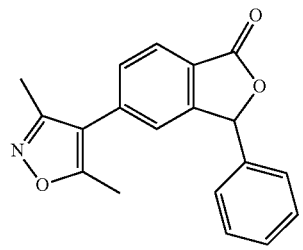 [SMILES: Cc1noc(C)c1-c1ccc2c(c1)C(c1ccccc1)OC2=O]

Reaction scheme:

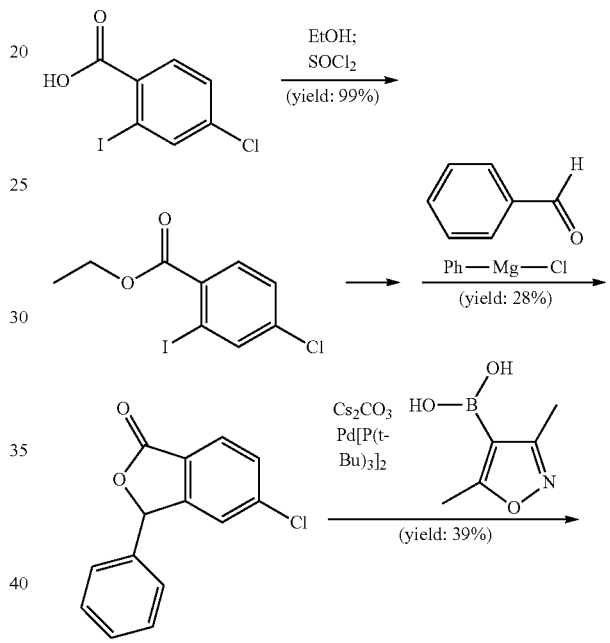

4-Chloro-2-iodo-benzoic acid ethyl ester

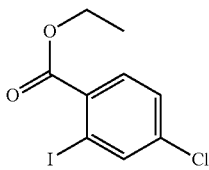

Analogue to the procedure described for 4-Bromo-2-iodo-benzoic acid ethyl ester.

Yield: 99% (2.2 g; 7.03 mmol)

HPLC-MS: (M+H)$^+$=311/313; $t_{Ret}$=2.22 min; AM8

5-Chloro-3-phenyl-3,1-isobenzofuran-1-one

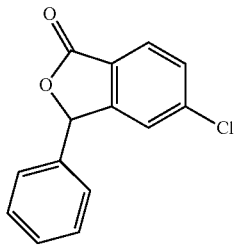 [SMILES: O=C1OC(c2ccccc2)c2cc(Cl)ccc21]

To a −78° C. solution of 4-Chloro-2-iodo-benzoic acid ethyl ester (250 mg; 0.81 mmol) in anhydrous tetrahydrofuran (2.5 ml) is dropped a 2.0 mol/l phenylmagnesium chloride (443 µl; 0.89 mmol) solution and stirred for 20 minutes. Benzaldehyde (164 µl; 1.61 mmol) is added at −78° C. and then stirred for 30 minutes at ambient temperature. The reaction mixture is quenched with 1 N HCl and extracted with methylene dichloride. The organic phase is dried over MgSO$_4$ and purified by using reversed phase chromatography under basic conditions.

Yield: 28% (55 mg; 0.23 mmol)
HPLC-MS: (M+H)$^+$=245; $t_{Ret}$=1.23 min; AM1

5-(3,5-Dimethyl-isoxazol-4-yl)-3-phenyl-3H-isobenzofuran-1-one

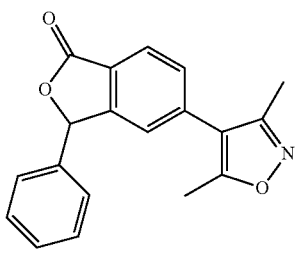 [SMILES: Cc1noc(C)c1-c1ccc2c(c1)C(c1ccccc1)OC2=O]

Analogue to the procedure described for 5-(3,5-Dimethyl-isoxazol-4-yl)-2-methyl-3-phenyl-2,3-dihydro-isoindol-1-one.

Yield: 39% (13 mg; 0.04 mmol)
HPLC-MS: (M+H)$^+$=306; $t_{Ret}$=1.21 min; AM1

Example 14

Preparation of 8-(3,5-Dimethyl-isoxazol-4-yl)-9b-phenyl-2,3-dihydro-9bH-oxazolo[2,3-a]isoindol-5-one

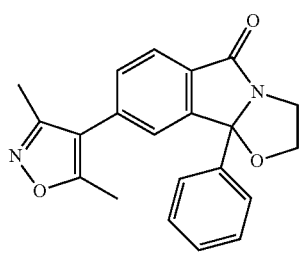 [SMILES: Cc1noc(C)c1-c1ccc2c(c1)C1(c3ccccc3)OCCN1C2=O]

Reaction scheme:

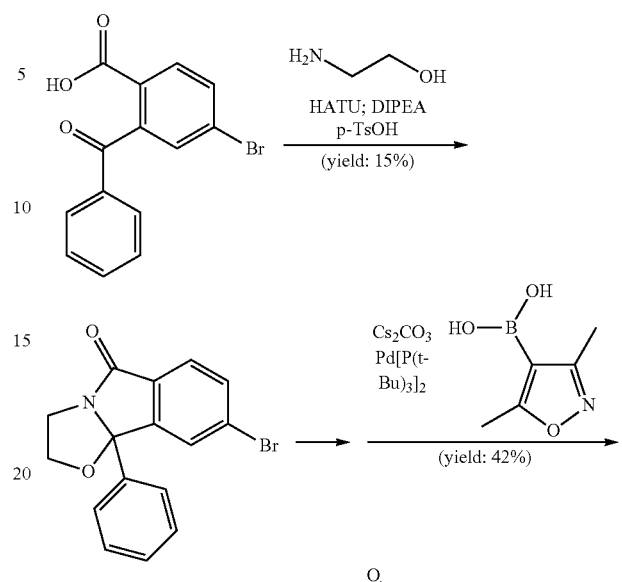

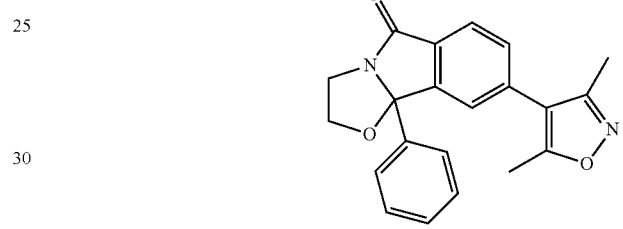

2-Benzoyl-4-bromo-benzoic acid

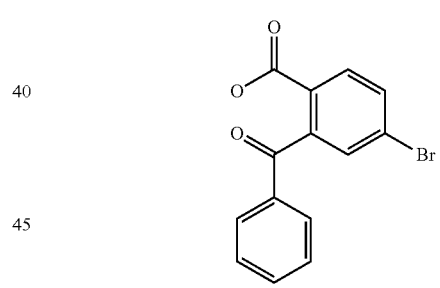

Analogue to the procedure described for 4-Bromo-2-(3-fluoro-5-methoxy-benzoyl)-benzoic acid Yield: 97% (289 mg; 0.98 mmol)
HPLC-MS: (M−H)$^−$=303/305; $t_{Ret}$=1.98 min; AM8

8-Bromo-9b-phenyl-2,3-dihydro-9bH-oxazolo[2,3-a]isoindol-5-one

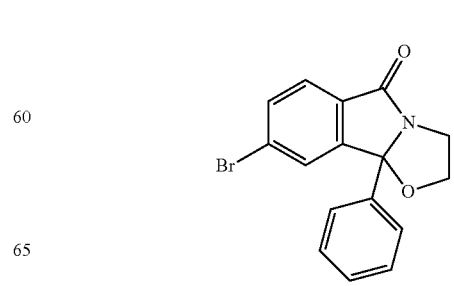

To a solution of 2-Benzoyl-4-bromo-benzoic acid (100 mg; 0.33 mmol) in N,N-dimethylformamide (1 ml) with N,N-Diisopropylethylamine (127 µl; 0.98 mmol) is added HATU (137 mg; 0.36 mmol). It is stirred at ambient temperature for 5 minutes before ethanolamine (21 µl; 0.33 mmol) is added. After 4 hours the reaction mixture is purified via reversed phase chromatography under basic conditions. The received 5-Bromo-3-hydroxy-2-(2-hydroxy-ethyl)-3-phenyl-2,3-dihydro-isoindol-1-one is taken up in 1 ml toluene and treated with p-Toluenesulfonic acid monohydrate (3 mg; 0.02 mmol) at 120° C. for 2 days. It is purified via reversed phase chromatography under basic conditions.

Yield: 15% (16 mg; 0.05 mmol)

HPLC-MS: (M+H)$^+$=330/332; $t_{Ret}$=1.85 min; AM9

8-(3,5-Dimethyl-isoxazol-4-yl)-9b-phenyl-2,3-dihydro-9bH-oxazolo[2,3-a]isoindol-5-one

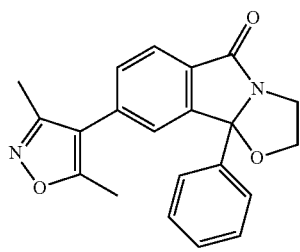 [SMILES: Cc1noc(C)c1-c1ccc2c(c1)C1(c3ccccc3)OCCN1C2=O]

Analogue to the procedure described for 5-(3,5-Dimethyl-isoxazol-4-yl)-2-methyl-3-phenyl-2,3-dihydro-isoindol-1-one.

Yield: 42% (7 mg; 0.02 mmol)

HPLC-MS: (M+H)$^+$=347; $t_{Ret}$=1.21 min; AM1

Example 15

Preparation of 9-(3,5-Dimethyl-isoxazol-4-yl)-10b-phenyl-3,4-dihydro-2H,10bH-[1,3]oxazino[2,3-a]isoindol-6-one

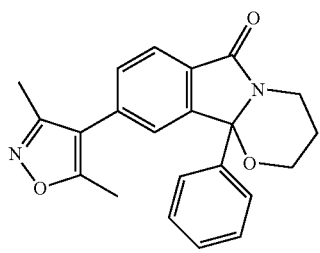

Prepared using a procedure analogous to the procedure described for 8-(3,5-Dimethyl-isoxazol-4-yl)-9b-phenyl-2,3-dihydro-9bH-oxazolo[2,3-a]isoindol-5-one Yield: 72% (57 mg; 0.16 mmol)

HPLC-MS: (M+H)$^+$=361; $t_{Ret}$=1.22 min; AM1

Example 16

Preparation of 5-(3,5-Dimethyl-isoxazol-4-yl)-4-methyl-3-phenyl-3,1-isobenzofuran-1-one

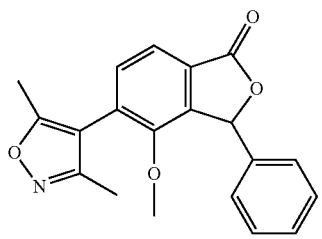 [SMILES: COc1c(-c2c(C)noc2C)ccc2c1C(c1ccccc1)OC2=O]

Reaction scheme:

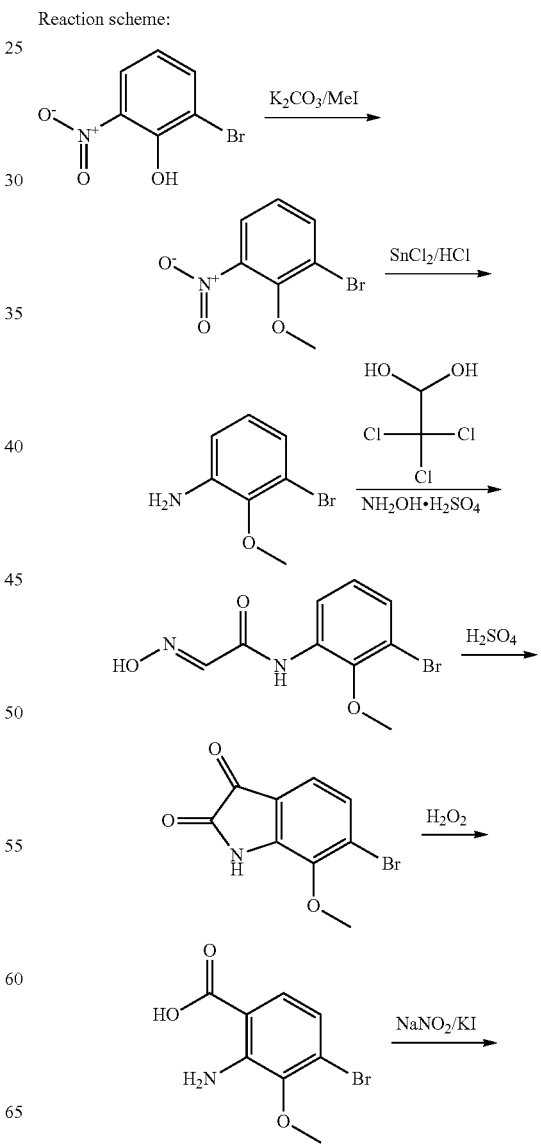

41
-continued

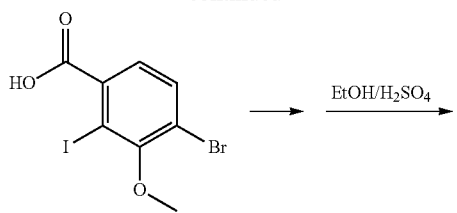

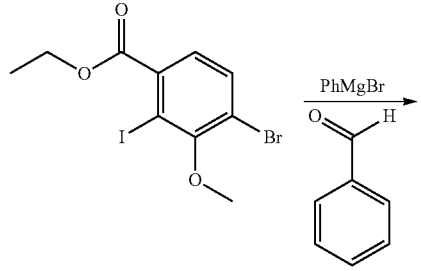

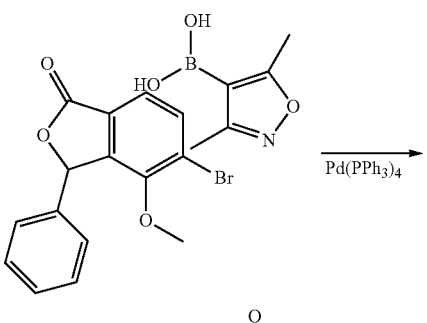

1-Bromo-2-methoxy-3-nitro-benzene

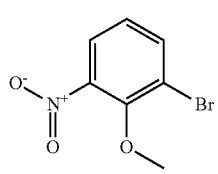

A mixture of 2-Bromo-6-nitro-phenol (43.6 g, 0.2 mol), K$_2$CO$_3$ (82.9 g, 0.6 mol), acetone (600 mL) is stirred at 70° C. for 1 h. Then MeI (85.14 g, 0.6 mol) is slowly added to the reaction mixture and refluxed for 8 h. After reaction, filtered and the filtrate is extracted with ethyl acetate (3×1000 mL). The combined SnCl2 organic phase is washed with water and brine, dried over Na$_2$SO$_4$, concentrated in vacuo to obtain the desired product.

Yield: 44 g (95%)

HPLC-MS: M+H=232/234; t$_{Ret}$=2.04 min; AM12

42
3-Bromo-2-methoxy-phenylamine

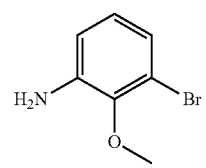

A mixture of 1-Bromo-2-methoxy-3-nitro-benzene (17.8 g, 0.0768 mol), SnCl$_2$ (69.27 g, 0.3069 mol) and 4N HCl (80 mL) in THF (200 mL) is stirred at 80° C. for 16 h. After reaction, evaporated out THF and added NaHCO$_3$ solution, filtered and the filtrate is extracted with ethyl acetate (3×800 mL). The combined organic phase is ished with water and brine, dried over Na$_2$SO$_4$, concentrated in vacuo to give the desired product. Yield: 14.8 g (96%).

HPLC-MS: M+H=202/204; t$_{Ret}$=1.49 min; AM12

N-(3-Bromo-2-methoxy-phenyl)-2-hydroxyimino-acetamide

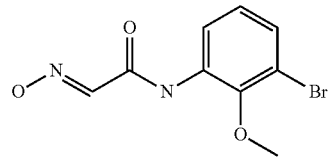

A mixture of 3-Bromo-2-methoxy-phenylamine (10 g, 0.05 mol), NH$_2$OH.H$_2$SO$_4$ (48.73 g, 0.3 mol), conc. HCl (5 mL) in H$_2$O (50 mL) is slowly added to the solution of chloral hydrate (9 g, 0.05 mol), Na$_2$SO$_4$ (42.18 g, 0.3 mol) in H$_2$O (200 mL) then stirred at 35° C. for 1 h, 52° C. for 1.5 h, 75° C. for 1 h. After the reaction, the mixture is filtered and the solid is dried under vacuum to give the desired compound.

Yield: 12.7 g (94%)

HPLC-MS: M+H=273/275; t$_{Ret}$=1.65 min; AM12

6-Bromo-7-methoxy-1H-indole-2,3-dione

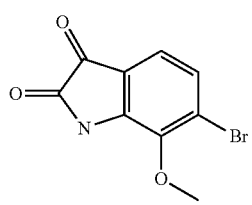

A mixture of N-(3-Bromo-2-methoxy-phenyl)-2-hydroxy-imino-acetamide (36 g, 0.132 mol), conc.H$_2$SO$_4$ (193 mL) is stirred at 80° C. for 1 hour. After reaction, poured the reaction mixture into ice water (2 L). The mixture is filtered and the solid is dried under vacuum to give the desired product.

Yield: 25 g (74%).

HPLC-MS: M+H=256/258; t$_{Ret}$=1.67 min; AM12

2-Amino-4-bromo-3-methoxy-benzoic acid

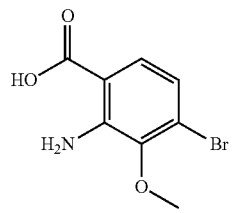

H$_2$O$_2$ (37%, 7.7 mL, 0.075 mol) in H$_2$O (70 mL) is slowly added to the solution of 6-Bromo-7-methoxy-1H-indole-2,3-dione (8.0 g, 0.0312 mol), NaOH (8.8 g, 0.219 mol) in H$_2$O (200 mL) then stirred at room temperature for 1 hour. After reaction, the mixture is filtered and the solid is dried under vacuum to give the desired product.

Yield: 5.4 g (70%)

HPLC-MS: M+H=244/246; t$_{Ret}$=0.55 min; AM4

4-Bromo-2-iodo-3-methoxy-benzoic acid

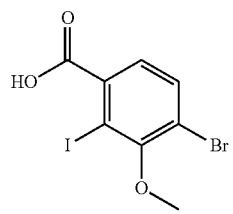

A mixture of 2-Amino-4-bromo-3-methoxy-benzoic acid (13.0 g, 0.0528 mol), conc.H$_2$SO$_4$ (17.2 mL) and H$_2$O (120 mL) is cooled to 5° C., then NaNO$_2$ (4.37 g, 0.0634 mol) in H$_2$O (20 mL) is slowly added to the mixture at 5° C. and stirred at this temperature for 1 hour. Then KI (26.24 g, 0.1585 mol) is added slowly to the reaction mixture at 5° C. and then refluxed for 8 h. The mixture is filtered and the red solid is washed with hexane to give the desired product.

Yield: 14.23 g (76%)

HPLC-MS: M+H=357/359; t$_{Ret}$=1.85 min; AM12

4-Bromo-2-iodo-3-methoxy-benzoic acid ethyl ester

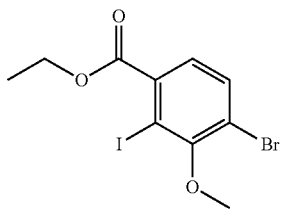

A mixture of 4-Bromo-2-iodo-3-methoxy-benzoic acid (12.0 g, 0.0336 mol) and conc.H$_2$SO$_4$ (20 mL) in EtOH (200 mL) is refluxed overnight. After reaction, evaporated out EtOH and the mixture is extracted with ethyl acetate (3×1000 mL). The combined organic phase is washed with water and brine, dried over Na$_2$SO$_4$, concentrated in vacuo, purified by column chromatography on silica gel eluted with petroleum ether/ethyl acetate=20:1 to afford the desired product as a colourless oil.

Yield: 10.9 g (84%)

HPLC-MS: M+H=387/389; t$_{Ret}$=3.12 min; AM7

5-Bromo-4-methoxy-3-phenyl-3,1-isobenzofuran-1-one

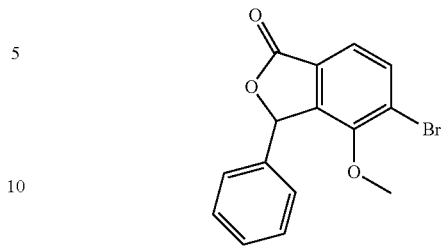

A mixture of 4-Bromo-2-iodo-3-methoxy-benzoic acid ethyl ester (0.3 g, 0.78 mmol), LiCl (0.033 g, 0.78 mmol) in THF (10 mL) is cooled to −10° C. under nitrogen, then PhMgBr (3N, 0.3 mL) is slowly added to the reaction mixture and stirred at −10° C. for 2 h under nitrogen. Benzaldehyde (0.165 g, 1.56 mmol) is slowly added to the reaction mixture at −10° C. under nitrogen, then stirred at room temperature under nitrogen for 16 hours. After reaction, evaporated out THF, purified by column chromatography on silica gel eluted with petroleum ether and ethyl acetate to afford the desired product.

Yield: 0.17 g (77%)

HPLC-MS: M+H=319/321; t$_{Ret}$=2.22 min; AM12

5-(3,5-Dimethyl-isoxazol-4-yl)-4-methoxy-3-phenyl-3,1-isobenzofuran-1-one

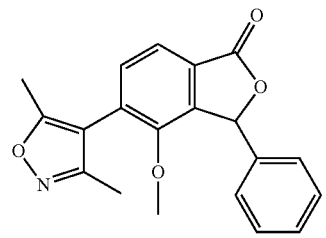 [SMILES: COc1c(-c2c(C)noc2C)ccc2c1C(c1ccccc1)OC2=O]

A mixture of 5-Bromo-4-methoxy-3-phenyl-3H-isobenzofuran-1-one (0.17 g, 0.533 mmol), 3,5-dimethylisoxazole-4-boronic acid (150 mg, 1.065 mmol), Na$_2$CO$_3$ (1N, 1.1 mL), Pd (PPh$_3$)$_4$ (62 mg, 0.0533 mmol) in dioxane (20 mL) is refluxed for 16 h. After reaction, evaporated out dioxane and purified by column chromatography on silica gel eluted with petroleum ether and ethyl acetate to afford the desired compound.

Yield: 0.14 g (78%)

HPLC-MS: M+H=336; t$_{Ret}$=3.02 min; AM5

Example 17

Preparation of 5-(3,5-Dimethyl-isoxazol-4-yl)-4-methyl-3-phenyl-3H-isobenzofuran-1-one

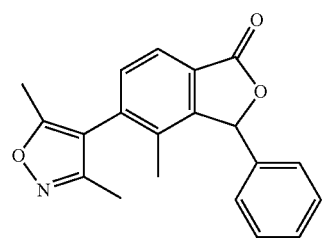 [SMILES: Cc1noc(C)c1-c1ccc2c(c1C)C(c1ccccc1)OC2=O]

Reaction scheme

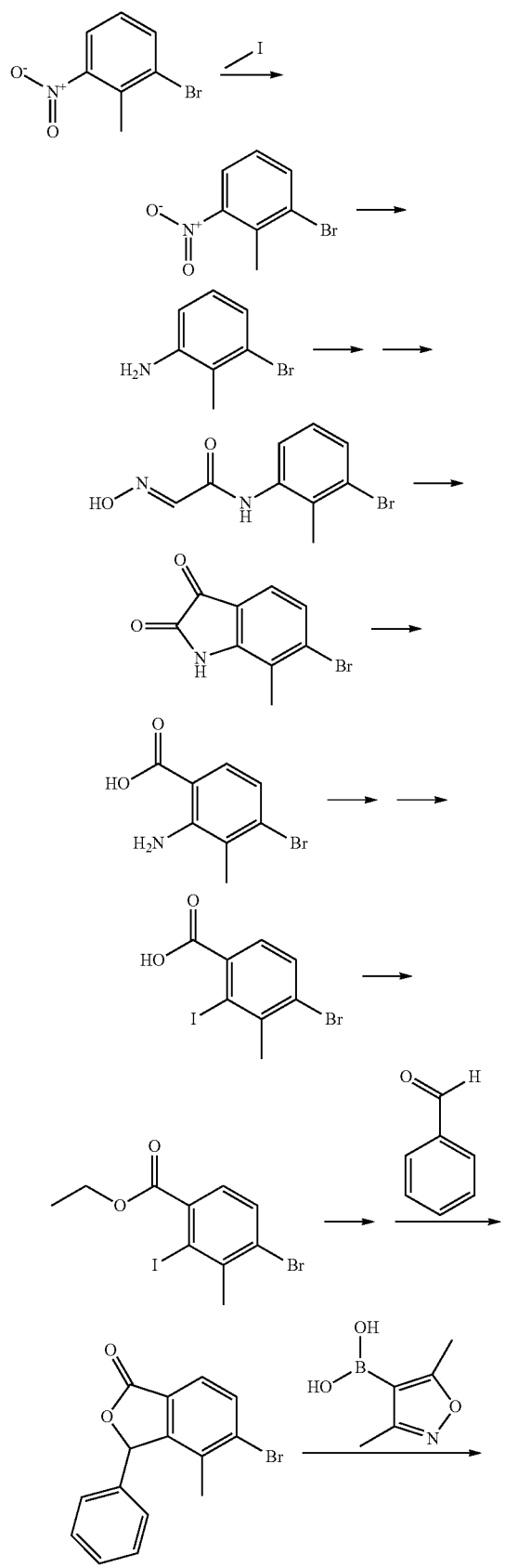

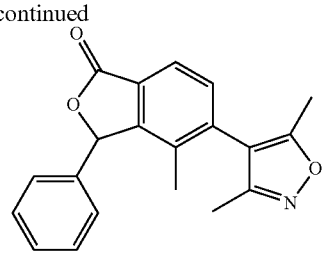

3-Bromo-2-methyl-phenylamine

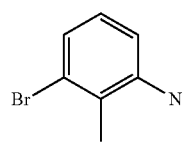

To a mixture of compound I-Bromo-2-methyl-3-nitro-benzene (2.0 g, 9.26 mmol) in EtOH (20 mL) and saturated NH₄Cl aqueous solution (5 mL) is added iron power (2.6 g, 46.2 mmol, 5 eq) at 50° C. in portions. Then the reaction is stirred for 4 h at 70° C. After filtration, the filtrate is concentrated. The residue mixture is extracted with EtOAc, washed with water and brine. The organic layer is dried over anhydrous Na₂SO₄, filtered and concentrated to give the desired compound.

Yield: 1.6 g (94%)

TLC (5:1, petrol ether/ethyl acetate) Rf=0.2

N-(3-Bromo-2-methyl-phenyl)-2-hydroxyimino-acetamide

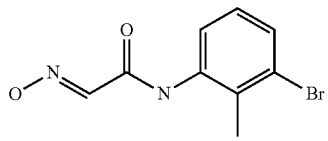

A mixture of 3-Bromo-2-methyl-phenylamine (15.6 g, 0.084 mol), NH₂OH H₂SO₄ (71.25 g, 0.5 mol), conc. HCl (8.8 mL) in H₂O (90 mL) is slowly added to a solution of chloral hydrate (15.2 g, 0.09 mol), Na₂SO₄ (71.25 g, 0.44 mol) in H₂O (255 mL) then stirred at 35° C. for 1 h, 52° C. for 1.5 h, 75° C. for 1 h. After the reaction, the mixture is filtered and the solid is dried under vacuum to give product.

Yield: 18 g (83%)

6-Bromo-7-methyl-1H-indole-2,3-dione

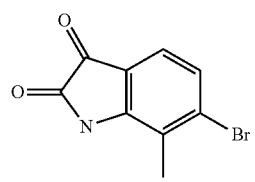

A mixture of N-(3-Bromo-2-methyl-phenyl)-2-hydroxy-imino-acetamide (18.0 g, 0.07 mol), conc.H₂SO₄ (150 mL) is stirred at 80° C. for 1 h. After reaction, poured the reaction mixture to ice water (2 L) the mixture is filtered and the solid is dried under vacuum to give product.

Yield: 8.4 g (50%)

2-Amino-4-bromo-3-methyl-benzoic acid

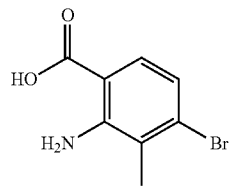

H$_2$O$_2$ (37%, 9.5 mL, 0.075 mol) in H$_2$O (83 mL) is slowly added to a solution of 6-Bromo-7-methyl-1H-indole-2,3-dione (8.4 g, 0.035 mol) and NaOH (9.6 g, 0.24 mol) in H$_2$O (185 mL) then stirred at room temperature for 1 h, After reaction, the mixture is filtered and the solid is dried under vacuum to give product.

Yield: 5.24 g (65%)

4-Bromo-2-iodo-3-methyl-benzoic acid

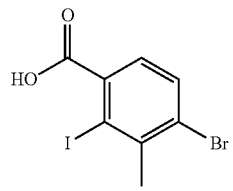

A mixture of 2-Amino-4-bromo-3-methyl-benzoic acid (5.24 g, 0.028 mol), conc.H$_2$SO$_4$ (7.51 mL) and H$_2$O (50 mL) is cooled to 5° C. NaNO$_2$ (1.89 g, 0.0274 mol) in H$_2$O (10 mL) is slowly added to the mixture and stirred at 5° C. for 2 h. KI (11.35 g, 0.0684 mol) is slowly added to the reaction mixture at 5° C. and then refluxed for 8 h. The mixture is filtered and the red solid is washed with hexane to give product.

Yield: 5.43 g (70%)

HPLC-MS: M+H=339/341; t$_{Ret}$=0.87 min; AM4

4-Bromo-2-iodo-3-methyl-benzoic acid ethyl ester

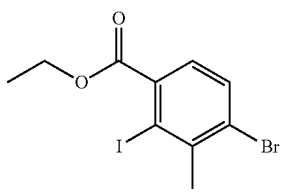

A mixture of 4-Bromo-2-iodo-3-methyl-benzoic acid (5.43 g, 0.016 mol) and conc.H$_2$SO$_4$ (5 mL) in EtOH (50 mL) is refluxed overnight. After reaction, evaporated out EtOH, extracted with ethyl acetate (3×50 mL), The combined organic phase is washed with water and brine, dried over Na$_2$SO$_4$, concentrated in vacuo, and purified by column chromatography on silica gel eluted with petrol ether and ethyl acetate to afford the desired compound. Yield: 5.2 g (88%)

HPLC-MS: M+H=369/371; t$_{Ret}$=3.43 min; AM7

5-Bromo-4-methyl-3-phenyl-3H-isobenzofuran-1-one

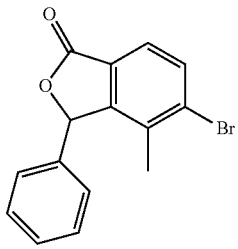 [SMILES: Cc1c(Br)ccc2c1C(c1ccccc1)OC2=O]

3M PhMgBr in diethyl ether (1.7 mL, 5.07 mmol, 1.1 eq.) is added dropwise to the solution of 4-Bromo-2-iodo-3-methyl-benzoic acid ethyl ester (1.7 g, 4.61 mmol), LiCl (195 mg, 4.61 mmol) in dry THF (50 mL) at −10° C. The mixture is stirred at −10° C. for 2 hours. Benzaldehyde (0.977 g, 9.22 mmol) is slowly added to mixture at −10° C. This solution is stirred at room temperature for 16 hours and diluted with saturated aqueous ammonium chloride solution (100 mL). This solution is extracted with ethyl acetate (3×70 mL). The combined organic layers are washed with water and brine, dried over anhydrous sodium sulfate, concentrated in vacuo. The residue is purified by a silica chromatography to give the desire compound as a white solid.

Yield: 720 mg (51%)

HPLC-MS: M+H=303/305; t$_{Ret}$=3.26 min; AM5

5-(3,5-Dimethyl-isoxazol-4-yl)-4-methyl-3-phenyl-3H-isobenzofuran-1-one

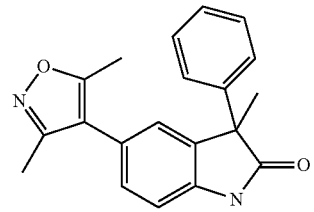 [SMILES: Cc1noc(C)c1-c1ccc2c(c1)C(C)(c1ccccc1)C(=O)N2]

A mixture of 5-Bromo-4-methyl-3-phenyl-3H-isobenzofuran-1-one (100 mg, 0.33 mmol), 3,5-dimethylisoxazole-4-boronic acid (93 mg, 0.66 mmol, 2 eq.), 1N Na$_2$CO$_3$ (0.66 mL, 0.66 mmol) and Pd(PPh$_3$)$_4$ (62 mg, 0.033 mmol, 0.1 eq.) in dioxane (20 mL) is stirred at 90° C. for 16 hours. After cooled to room temperature, the mixture is evaporated in vacuo. The residue is purified by preparative-TLC using a petrol ether ethyl acetate mixture to afford the desired compound as a white solid.

Yield: 60 mg (57%)

HPLC-MS: M+H=320; t$_{Ret}$=3.02 min; AM5

Example 18

Preparation of 5-(3,5-Dimethyl-isoxazol-4-yl)-3-methyl-3-phenyl-1,3-dihydro-indol-2-one Reaction scheme:

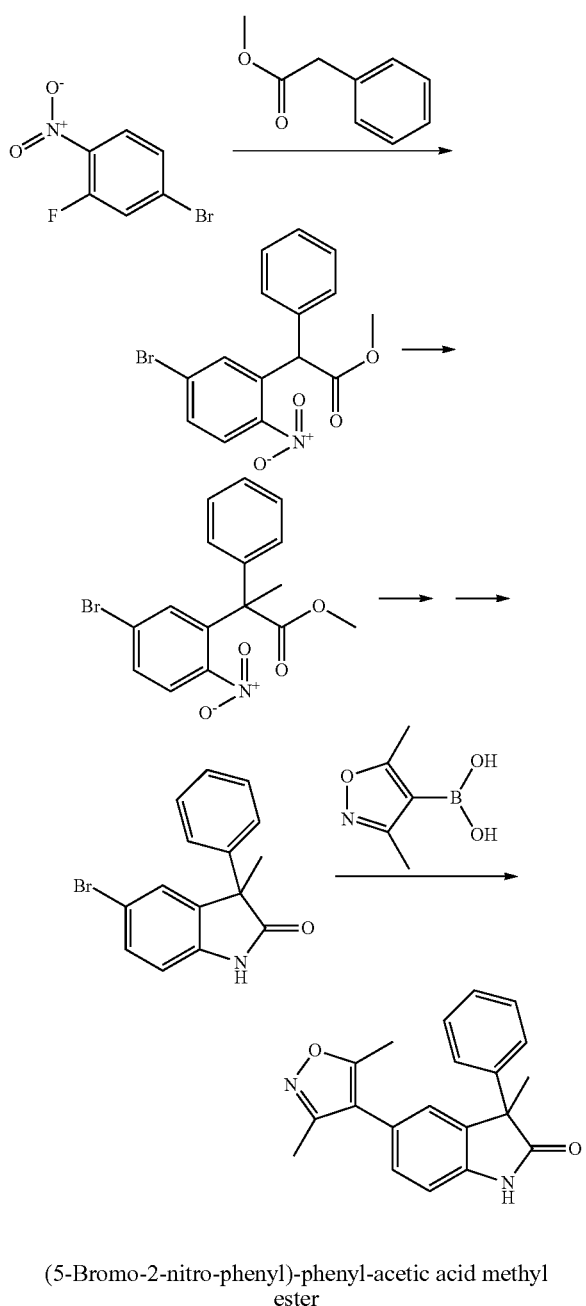

(5-Bromo-2-nitro-phenyl)-phenyl-acetic acid methyl ester

NaH (1.6 g, 63 mmol) is added portion wise to a solution of phenyl-acetic acid methyl ester (9.0 g, 60 mmol) in DMF (150 mL) at −15° C. and stirred at this temperature for 3 hours. 4-Bromo-2-fluoro-1-nitro-benzene (6.57 g, 30.0 mmol) is added to the above mixture at −15° C. The mixture is warmed to room temperature slowly and stirred for 24 hours. The mixture is diluted with saturated aqueous NH₄Cl solution and extracted with ethyl acetate (3×100 mL). The combined organic phase is washed with water and brine, dried over Na₂SO₄, filtered and concentrated. The residue is purified by chromatography (ethyl acetate:petroleum ether=1:20) to give the desired product.

Yield: 6.8 g (65%)

2-(5-Bromo-2-nitro-phenyl)-2-phenyl-propionic acid methyl ester

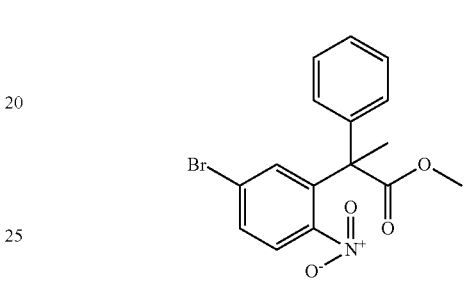

NaH (562 mg, 23.4 mmol) is added portion wise to a solution of (5-Bromo-2-nitro-phenyl)-phenyl-acetic acid methyl ester (6.8 g, 19.5 mmol) in DMF (100 mL) at room temperature and stirred at room temperature for 3 hours. MeI (8.3 g, 58.5 mmol) is added to the above mixture at 0° C. The mixture is warmed to room temperature slowly and stirred overnight. The mixture is diluted with saturated aqueous NH₄Cl solution and extracted with ethyl acetate (3×100 mL). The combined organic phase is washed with water and brine, dried over Na₂SO₄, filtered and concentrated to give the product.

Yield: 6.0 g (86%).

HPLC-MS: M+H=365/367; $t_{Ret}$=2.18 min; AM12

5-Bromo-3-methyl-3-phenyl-1,3-dihydro-indol-2-one

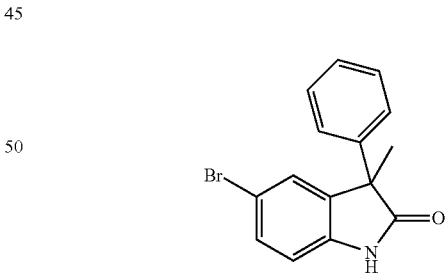

A mixture of 2-(5-Bromo-2-nitro-phenyl)-2-phenyl-propionic acid methyl ester (5.9 g, 16.25 mmol) and iron powder (3.64 g, 65 mmol) in acetic acid (100 mL) is heated to 70° C. and stirred for 3 hours. The acetic acid is removed in vacuo. The residue is diluted with satu. aq. NH₄Cl solution and extracted with ethyl acetate (3×100 mL). The combined organic phase is washed with water and brine, dried over Na₂SO₄, filtered and concentrated. The residue is recrystallized by ethyl acetate to give the desired product. Yield: 3.5 g (71%)

HPLC-MS: M+H=302/304; $t_{Ret}$=3.06 min; AM5

5-(3,5-Dimethyl-isoxazol-4-yl)-3-methyl-3-phenyl-1,3-dihydro-indol-2-one

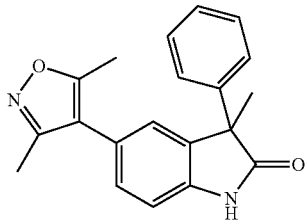 [SMILES: Cc1noc(C)c1-c1ccc2c(c1)C(C)(c1ccccc1)C(=O)N2]

A mixture of 5-Bromo-3-methyl-3-phenyl-1,3-dihydro-indol-2-one (602 mg, 2 mmol), compound 3,5-dimethylisoxazole-4-boronic acid (564 mg, 4 mmol), Pd(PPh$_3$)$_4$ (440 mg, 0.4 mmol) and Cs$_2$CO$_3$ (1.624 g, 5 mmol) in dioxane (10 mL) and H$_2$O (5 mL) is stirred at 80° C. under nitrogen for 20 hours. The mixture is poured into water (20 mL) and extracted with ethyl acetate (20 mL×3). The combined organic phase is washed with water and brine, dried over Na$_2$SO$_4$, filtered and concentrated. The residue is purified by chromatography on silica gel (ethyl acetate:petroleum ether=1:2) to give the desired compound.

Yield: 140 mg (22%)

HPLC-MS: M+H=319; $t_{Ret}$=1.13 min; AM1

Example 19

Preparation of 5-(3,5-Dimethyl-isoxazol-4-yl)-1,3-dimethyl-3-phenyl-1,3-dihydro-indol-2-one

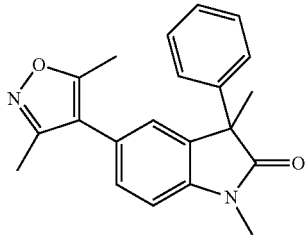 [SMILES: Cc1noc(C)c1-c1ccc2c(c1)C(C)(c1ccccc1)C(=O)N2C]

A mixture of 5-(3,5-Dimethyl-isoxazol-4-yl)-3-methyl-3-phenyl-1,3-dihydro-indol-2-one (54 mg, 0.196 mmol) and NaH (5.5 mg, 0.203 mmol) in THF (10 mL) is stirred at room temperature for 1.5 h. MeI (48 mg, 0.338 mmol) is added to the mixture and stirred overnight. The solvent is removed in vacuo. The residue is purified by chromatography (ethyl acetate:petroleum ether=1:2) to give the desired compound.

Yield: 30 mg (53%)

HPLC-MS: M+H=333; $t_{Ret}$=2.64 min; AM7

Example 20

Preparation of 5-(3,5-Dimethyl-isoxazol-4-yl)-3-methyl-3-phenyl-1-pyridin-3-yl-1,3-dihydro-indol-2-one

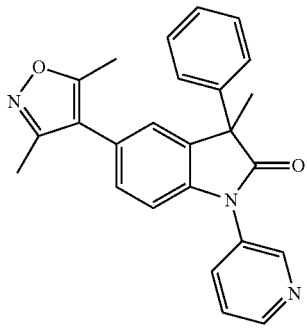 [SMILES: Cc1noc(C)c1-c1ccc2c(c1)C(C)(c1ccccc1)C(=O)N2c1cccnc1]

5-(3,5-Dimethyl-isoxazol-4-yl)-3-methyl-3-phenyl-1,3-dihydro-indol-2-one (100 mg, 0.314 mmol), 3-iodopyridine (71 mg, 0.346 mmol), copper (I) iodide (60 mg, 0.314 mmol), N,N'-dimethylethylenediamine (41.5 mg, 0.471 mmol), potassium carbonate (217 mg, 1.571 mmol) are added to a microwave vessel. Dioxane (5 mL) is added and the mixture heated to 140° C. for 30 minutes in a microwave reactor. A further 3-iodopyridine (35 mg, 0.173 mmol) and copper (I) iodide (12 mg, 0.063 mmol) are added. The mixture is again heated to 140° C. for 30 minutes in a microwave reactor. The reaction mixture is filtered. The filtrate is washed with dichloromethane. The volatiles are evaporated and the residue purified using reversed phase HPLC. This afforded the desired product.

Yield: 82 mg (66%)

HPLC-MS: M+H=396; $t_{Ret}$=1.23 min; AM1

Example 21

Preparation of 5-(3,5-Dimethyl-isoxazol-4-yl)-3-hydroxy-3-phenyl-1,3-dihydro-indol-2-one

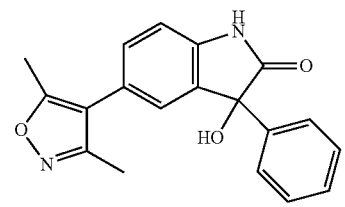 [SMILES: Cc1noc(C)c1-c1ccc2c(c1)C(O)(c1ccccc1)C(=O)N2]

3-Hydroxy-5-iodo-3-phenyl-1,3-dihydro-indol-2-one

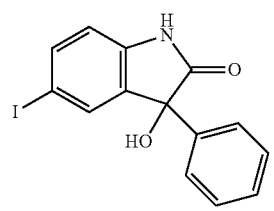 [SMILES: O=C1Nc2ccc(I)cc2C1(O)c1ccccc1]

A solution of 3M 2-methoxyphenylmagnesium bromide (0.92 mL, 2.747 mmol) in Et$_2$O is added drop wise to a suspension of 5-iodoisatin (300 mg, 1.099 mmol) in THF whilst cooling in ice. The mixture is then stirred at room temperature for 1 hour. The reaction mixture is quenched by adding ammonium chloride solution and extracted several times with ethyl acetate. The combined organic phases are washed several times with water, dried over MgSO$_4$ and concentrated under reduced pressure. The precipitate is filtered off with suction, washed with very small amounts of ethyl acetate and dried. This afforded the desired product as a light yellow solid.

Yield: 234 mg (66%)

HPLC-MS: M+H=334; $t_{Ret}$=1.08 min; AM1

5-(3,5-Dimethyl-isoxazol-4-yl)-3-hydroxy-3-phenyl-1,3-dihydro-indol-2-one

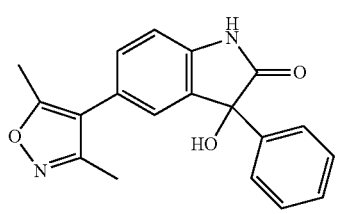 [SMILES: Cc1noc(C)c1-c1ccc2c(c1)C(O)(c1ccccc1)C(=O)N2]

3-Hydroxy-5-iodo-3-phenyl-1,3-dihydro-indol-2-one (130 mg, 0.370 mmol), 3,5-dimethyl-4-isoxazolylboronic acid (104 mg, 0.740 mmol), sodium carbonate (108 mg, 1.025 mmol), Pd(dppf)Cl$_2$ (57 mg, 78 mmol) and lithium chloride (114.5 mg, 2.700 mmol) are added to a microwave vial. Dioxane/water (2:1, 3 mL) is added. The mixture is flushed with argon and the vessel heated at 130° C. for 1 h. The reaction mixture is diluted with water and dcm then extracted with dcm. The organic layer is dried with Na$_2$SO$_4$, filtered and concentrated under reduced pressure. The residue is dissolved in DMSO, filtered and purified with the acidic (formic acid) RP HPLC system. The product containing fractions are concentrated under reduced pressure. Dissolved in DMSO, aliquoted and freeze dried. Once more freeze dried with acetonitril: water. This afforded the desired product.

Yield: 18.5 mg (15.6%)
HPLC-MS: M+H=321; t$_{Ret}$=0.98 min; AM1

Example 22

Preparation of 5-(3,5-Dimethyl-isoxazol-4-yl)-3-hydroxy-3-phenyl-1,3-dihydro-indol-2-one

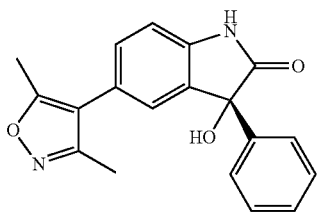 [SMILES: Cc1noc(C)c1-c1ccc2c(c1)[C@](O)(c1ccccc1)C(=O)N2]

Column: Daicel ChiralPak AD, 4.6×250 mm
Eluent: MeOH+0.1% DEA
Flow: 1 ml/min
Temperature: 40° C.

Example 23

Preparation of 5-(3,5-Dimethyl-isoxazol-4-yl)-3-hydroxy-3-(2-morpholin-4-ylmethyl-phenyl)-1,3-dihydro-indol-2-one

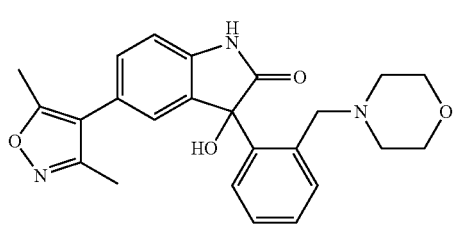 [SMILES: Cc1noc(C)c1-c1ccc2c(c1)C(O)(c1ccccc1CN1CCOCC1)C(=O)N2]

5-(3,5-Dimethyl-isoxazol-4-yl)-1H-indole-2,3-dione

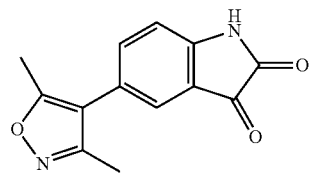 [SMILES: Cc1noc(C)c1-c1ccc2c(c1)C(=O)C(=O)N2]

5-iodo-1H-indole-2,3-dione (24.0 g, 83.5 mmol) and 2,5-dimethylisoxazole-4-boronic acid (16.0 g, 111.3 mmol) are dissolved in a mixture of water (400 mL) and 2-propanol (800 mL). Triethylamine (36.0 mL, 253.3 mmol) is added followed by 1,1-bis(diphenylphosphino)ferrocene-palladium(II) dichloride dichloromethane complex (1.0 g, 1.4 mmol). The mixture is purged with argon and then heated at reflux for 5 hours. The solvent is removed in vacuo and the residue partitioned between water and dichloromethane. The organic phase is dried over magnesium sulfate. And the volatiles removed in vacuo. The residue is purified by column chromatography on silica gel using a cyclohexane/ethyl acetate gradient. This afforded the desired product.

Yield: 3.65 g (17.7%)
HPLC-MS: M+H=243; t$_{Ret}$=0.78 min; AM1

5-(3,5-Dimethyl-isoxazol-4-yl)-3-hydroxy-3-(2-morpholin-4-ylmethyl-phenyl)-1,3-dihydro-indol-2-one

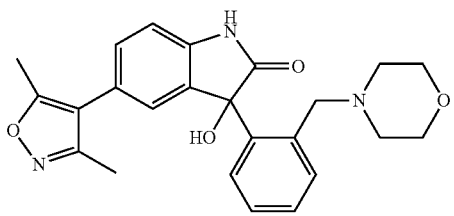 [SMILES: Cc1noc(C)c1-c1ccc2c(c1)C(O)(c1ccccc1CN1CCOCC1)C(=O)N2]

5-(3,5-Dimethyl-isoxazol-4-yl)-1H-indole-2,3-dione (100 mg, 0.41 mmol) is dissolved in anhydrous THF (1 mL) and cooled to 0° C. (2-(4-Morpholinylmethyl)phenyl)magnesium bromide (4.0 mL, 1.0 mmol) is added dropwise and then the mixture stirred at room temperature for 2 hours. The mixture is poured onto saturated aqueous ammonium chloride solution. The aqueous phase is extracted with ethyl acetate. The organic phase is dried over magnesium sulfate. The solvent is concentrated to dryness and purified using column chromatography on silica gel using a cyclohexane/ethyl acetate gradient. The product fractions are combined and concentrated to dryness in vacuo.

Yield: 40 mg (23%)
HPLC-MS: M+H=420; t$_{Ret}$=1.05 min; AM1

Example 24

Preparation of 5-(3,5-Dimethyl-isoxazol-4-yl)-3-hydroxy-3-(2-morpholin-4-ylmethyl-phenyl)-1,3-dihydro-indol-2-one

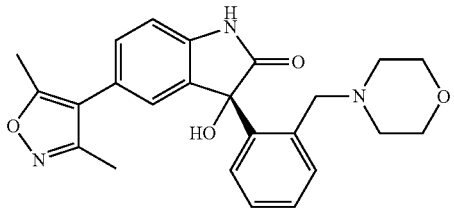 [SMILES: Cc1noc(C)c1-c1ccc2c(c1)[C@](O)(c1ccccc1CN1CCOCC1)C(=O)N2]

Column: Daicel ChiralPak AD, 4.6×250 mm
Eluent: MeOH+0.1% DEA

Flow: 1 ml/min
Temperature: 40° C.

Using an analogous method the compounds below are synthesised.

| Ex # | Structure | Name | Yield [%] | HPLC-MS (AM1): |
|---|---|---|---|---|
| 25 | 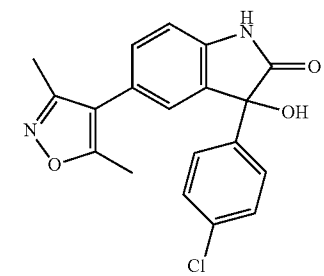 [SMILES: Cc1noc(C)c1-c1ccc2c(c1)C(O)(c1ccc(Cl)cc1)C(=O)N2] | 3-(4-Chloro-phenyl)-5-(3,5-dimethyl-isoxazol-4-yl)-3-hydroxy-1,3-dihydro-indol-2-one | 74 | M + H$^+$ = 355<br>$t_{Ret}$ = 1.08 min |
| 26 | 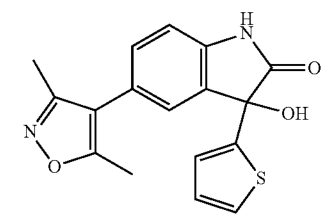 [SMILES: Cc1noc(C)c1-c1ccc2c(c1)C(O)(c1cccs1)C(=O)N2] | 5-(3,5-Dimethyl-isoxazol-4-yl)-3-hydroxy-3-thiophen-2-yl-1,3-dihydro-indol-2-one | 71 | M + H$^+$ = 327<br>$t_{Ret}$ = 0.92 min |
| 27 | 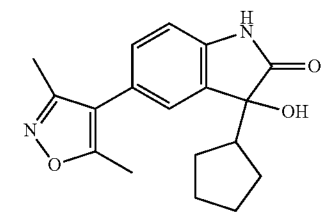 [SMILES: Cc1noc(C)c1-c1ccc2c(c1)C(O)(C1CCCC1)C(=O)N2] | 3-Cyclopentyl-5-(3,5-dimethyl-isoxazol-4-yl)-3-hydroxy-1,3-dihydro-indol-2-one | 70 | M + H$^+$ = 313<br>$t_{Ret}$ = 0.99 min |
| 28 | 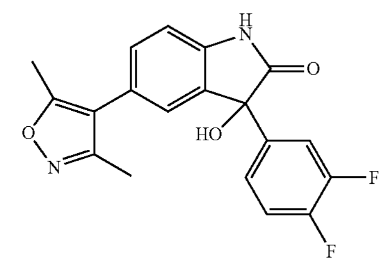 [SMILES: Cc1noc(C)c1-c1ccc2c(c1)C(O)(c1ccc(F)c(F)c1)C(=O)N2] | 3-(3,4-Difluoro-phenyl)-5-(3,5-dimethyl-isoxazol-4-yl)-3-hydroxy-1,3-dihydro-indol-2-one | 41 | M + H$^+$ = 357<br>$t_{Ret}$ = 1.04 min |
| 29 | 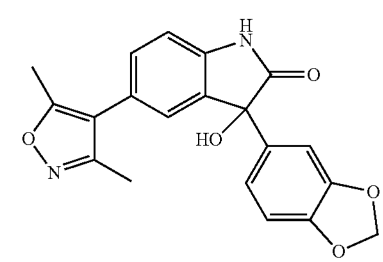 [SMILES: Cc1noc(C)c1-c1ccc2c(c1)C(O)(c1ccc3c(c1)OCO3)C(=O)N2] | 3-Benzo[1,3]dioxol-5-yl-5-(3,5-dimethyl-isoxazol-4-yl)-3-hydroxy-1,3-dihydro-indol-2-one | 38 | M + H$^+$ = 365<br>$t_{Ret}$ = 0.94 min |
| 30 | 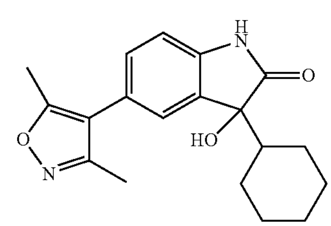 [SMILES: Cc1noc(C)c1-c1ccc2c(c1)C(O)(C1CCCCC1)C(=O)N2] | 3-cyclohexyl-5-(3,5-dimethyl-isoxazol-4-yl)-3-hydroxy-1,3-dihydro-indol-2-one | 33 | M + H$^+$ = 327<br>$t_{Ret}$ = 1.07 min |

| Ex # | Structure | Name | Yield [%] | HPLC-MS (AM1): |
|---|---|---|---|---|
| 31 | 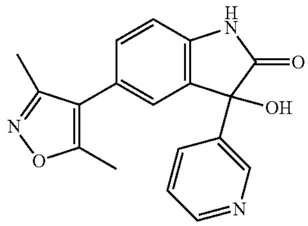 [SMILES: Cc1noc(C)c1-c1ccc2c(c1)C(O)(c1cccnc1)C(=O)N2] | 5-(3,5-Dimethyl-isoxazol-4-yl)-3-hydroxy-3-pyridin-3-yl-1,3-dihydro-indol-2-one | 38 | M + H$^+$ = 322<br>$t_{Ret}$ = 0.75 min |
| 32 | 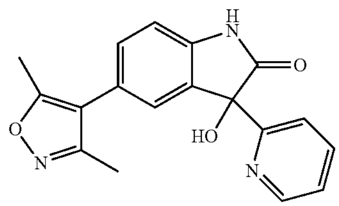 [SMILES: Cc1noc(C)c1-c1ccc2c(c1)C(O)(c1ccccn1)C(=O)N2] | 5-(3,5-Dimethyl-isoxazol-4-yl)-3-hydroxy-3-pyridin-2-yl-1,3-dihydro-indol-2-one | 55 | M + H$^+$ = 322<br>$t_{Ret}$ = 0.79 min |
| 33 | 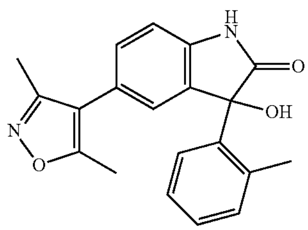 [SMILES: Cc1ccccc1C1(O)C(=O)Nc2ccc(-c3c(C)noc3C)cc21] | 5-(3,5-Dimethyl-isoxazol-4-yl)-3-hydroxy-3-o-tolyl-1,3-dihydro-indol-2-one | 57 | M + H$^+$ = 335<br>$t_{Ret}$ = 1.02 min |
| 34 | 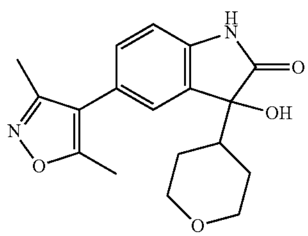 [SMILES: Cc1noc(C)c1-c1ccc2c(c1)C(O)(C1CCOCC1)C(=O)N2] | 5-(3,5-Dimethyl-isoxazol-4-yl)-3-hydroxy-3-(tetrahydro-pyran-4-yl)-1,3-dihydro-indol-2-one | 44 | M + H$^+$ = 329<br>$t_{Ret}$ = 0.77 min |
| 35 | 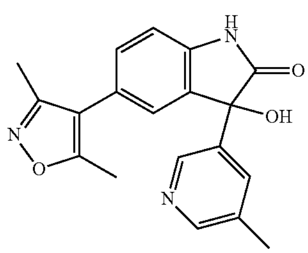 [SMILES: Cc1cncc(C2(O)C(=O)Nc3ccc(-c4c(C)noc4C)cc32)c1] | 5-(3,5-Dimethyl-isoxazol-4-yl)-3-hydroxy-3-(5-methyl-pyridin-3-yl)-1,3-dihydro-indol-2-one | 78 | M + H$^+$ = 336<br>$t_{Ret}$ = 0.83 min |

Biological Methods

BRD4-H4 tetraacetylated Peptide Inhibition AlphaScreen

This assay is used to determine whether the compounds inhibit the interaction between the first (BRD4-BD1) or the second (BRD4-BD2) bromodomain of BRD4 and the tetraacetylated histone H4 peptide.

Compounds are diluted in serial dilution 1:5 in assay buffer from 10 mM stock in DMSO (100 µM start concentration) in white OptiPlate-384 (PerkinElmer). A mix consisting of 15 nM GST-BRD4-BD1 protein (aa 44-168) or 150 nM GST-BRD4-BD2 (aa 333-460) and 15 nM biotinylated Acetyl-Histone H4 (LysS, 8, 12, 16) peptide is prepared in assay buffer (50 mM HEPES pH=7.4; 25 mM NaCl; 0.05% Tween 20; 0.1% bovine serum albumin (BSA); 10 mM dithiothreitol (DTT)). 6 µl of the mix is added to the compound dilutions. Subsequently, 6 µl of premixed AlphaLISA Glutathione Acceptor Beads and AlphaScreen Streptavidin Donor Beads from PerkinElmer (in assay buffer at a concentration of 10 µg/ml each) are added and the samples are incubated for 30 min at RT in the dark (shaking 300 rpm). Afterwards, the signal is measured in a PerkinElmer Envision HTS Multilabel Reader using the AlphaScreen protocol from PerkinElmer. Each plate contains negative controls where biotinylated Acetyl-Histone H4 peptide and GST-BRD4-BD1 or GST-BRD4-BD2 are left out and replaced by assay buffer. Negative control values are entered as low basis value when using the software GraphPad Prism for calculations. Furthermore, a positive control (probe molecule JQ1+ with protein/peptide mix) is pipetted. Determination of IC$_{50}$ values are carried out using GraphPad Prism 3.03 software (or updates thereof).

Table summarizing the IC$_{50}$ of the compounds of the invention exemplified above

| EX # | IC50 [nM] |
|---|---|
| 1 | 380 |
| 2 | 57 |
| 3 | 43 |
| 4 | 65 |
| 5 | 229 |
| 6 | 43 |
| 7 | 1094 |
| 8 | 55 |
| 9 | 14 |
| 10 | 38 |
| 11 | 2486 |
| 12 | 75 |
| 13 | 193 |
| 14 | 72 |
| 15 | 36 |
| 16 | 350 |
| 17 | 1082 |
| 18 | 54 |
| 19 | 275 |
| 20 | 242 |
| 21 | 259 |
| 22 | 48 |
| 23 | 176 |
| 24 | 41 |
| 25 | 295 |
| 26 | 320 |
| 27 | 698 |
| 28 | 203 |
| 29 | 541 |
| 30 | 196 |
| 31 | 395 |
| 32 | 332 |
| 33 | 1060 |
| 34 | 1572 |
| 35 | 1037 |

On the basis of their biological properties the compounds of general formula (1) according to the invention, their tautomers, racemates, enantiomers, diastereomers, mixtures thereof and the salts of all the above-mentioned forms are suitable for treating diseases characterised by virus infection, inflammatory diseases and abnormal cell proliferation, such as cancer.

For example, the following cancers may be treated with compounds according to to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma (MM)), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancers, which may be treated with compounds according to the invention, are hematopoietic malignancies (including but not limited to AML, MM), as well as solid tumors including but not limited to lung, liver, colon, brain, thyroid, pancreas, breast, ovary and prostate cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, to aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4,3-alethine, 131-1-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, to ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992(afatinib), BIBF 1120 (Vargatef), bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhu-MAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, Volasertib (or other polo-like kinae inhibitors), xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavouring enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I)

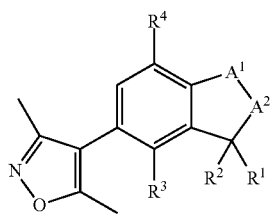

wherein,
A₁ is selected from —C=O and —NR⁵;
A₂ is selected from —O—, —C=O and —NR⁶;
R¹ is —H, —OH or —C$_{1-3}$alkyl;
R² is selected from phenyl, —C$_{5-8}$cycloalkyl, 5-6 membered heteroaryl, 6 to 9 membered heterocycle optionally and independently substituted with one or more R⁷;
R³ is —H, —C$_{1-3}$alkyl or —O—C$_{1-3}$alkyl;
R⁴ is —H or —C$_{1-3}$alkyl;
R⁵ is —H, —C$_{1-3}$alkyl or 6 membered heteroaryl;
R⁶ is —C$_{1-3}$alkyl, optionally substituted with —N(—C$_{1-3}$alkyl)₂, or R⁶ is 6 membered heterocycle;
or R¹ and R⁶ taken together form a 5-6 membered heterocycloalkyl;
R⁷ is selected from halogen, —O—C$_{1-3}$alkyl, —C$_{1-3}$ alkyl, which —C$_{1-3}$ alkyl can be optionally substituted with morpholine;
or a pharmaceutically acceptable salt thereof.

2. The compound according to claim 1, wherein A¹ is —C=O and A² is NR⁶, wherein R⁶ is —CH₃, —CH(CH₃)₂, —(CH₂)₂—N(CH₃)₂, —(CH₂)₃—N(CH₃)₂—N-methyl-piperidinyl.

3. The compound according to claim 1 wherein A¹ is NR⁵ and A² is —C=O, wherein R⁵ is —H, —CH₃ or pyridyl.

4. The compound according to claim 1 wherein A¹ is NR⁵ and A² is —O—.

5. The compound according to claim 1, wherein R¹ is —H, —OH, —CH₃.

6. The compound according to claim 1, wherein R² is phenyl, optionally substituted with one or more independently selected halogen, —CH₃, —O—CH₃ and —CH₂-morpholine.

7. The compound according to claim 1, wherein R² is cyclopentyl, cyclohexyl or spiro[3.5]nonane.

8. The compound according to claim 1, wherein R² is thiophenyl or pyridyl, optionally substituted with —CH₃ or tetrahydrofuran.

9. The compound according to claim 1, wherein R³ is —CH₃ or —OCH₃.

10. The compound according to claim 1, wherein R⁴ is —H or —CH₃.

11. The compound according to claim 1, wherein R⁵ is —H, —CH₃ or pyridyl.

12. The compound according claim 1, wherein A¹ is —C=O and A² is NR⁶, R⁶ and R¹ taken together form a oxazolidine or [1,3]oxazine.

13. A compound selected from

| EX# | Structure |
|---|---|
| 1 | 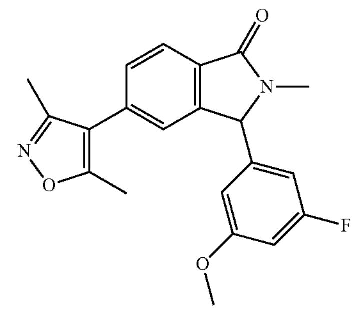 |
| 2 | 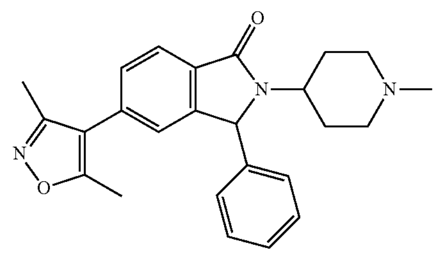 |
| 3 | 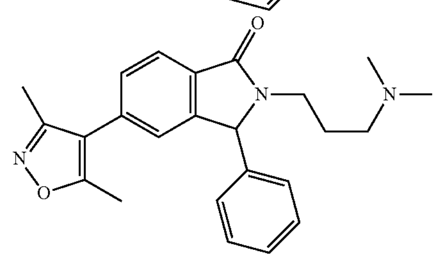 |
| 4 | 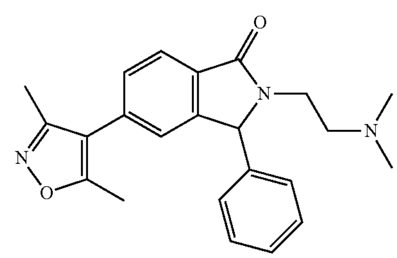 |
| 5 | 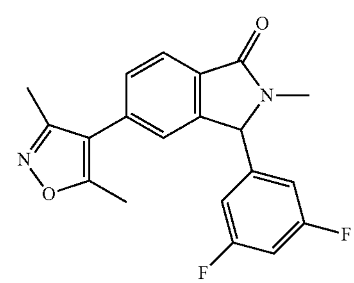 |
| 6 | 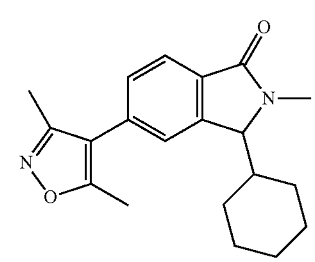 |

-continued
| EX# | Structure |
|---|---|
| 7 | 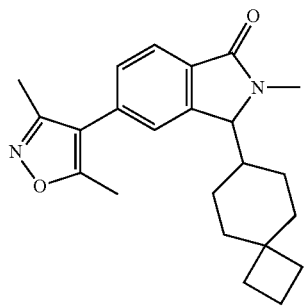 |
| 8 | 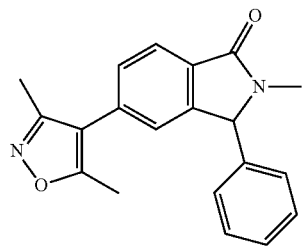 |
| 9 | 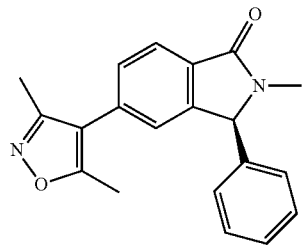 |
| 10 | 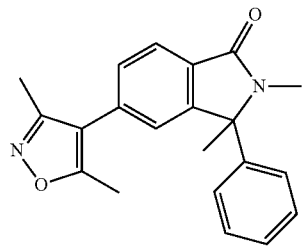 |
| 11 | 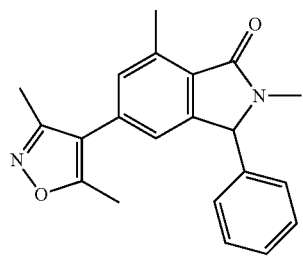 |
| 12 | 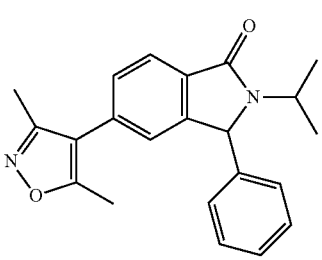 |
-continued
| EX# | Structure |
|---|---|
| 13 | 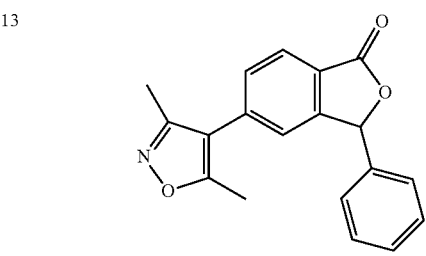 |
| 14 | 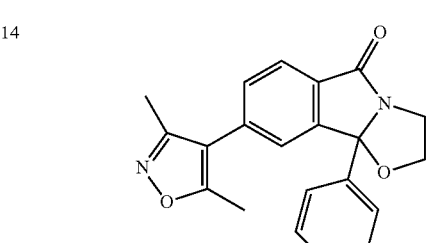 |
| 15 | 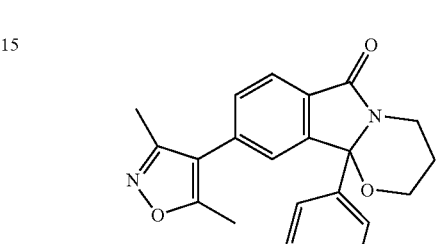 |
| 16 | 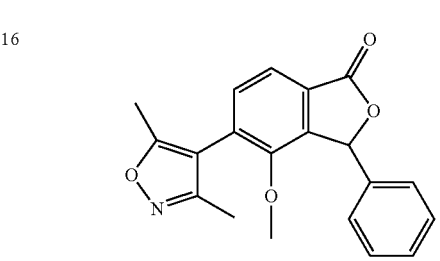 |
| 17 | 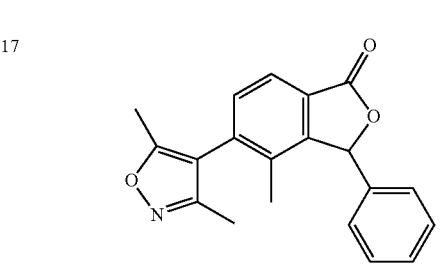 |
| 18 | 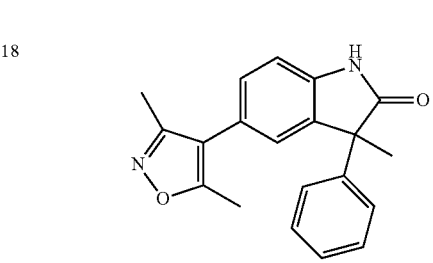 |

69
-continued
| EX# | Structure |
|---|---|
| 19 | 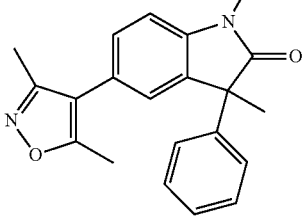 [SMILES: Cc1noc(C)c1-c1ccc2c(c1)C(C)(c1ccccc1)C(=O)N2] |
| 20 | 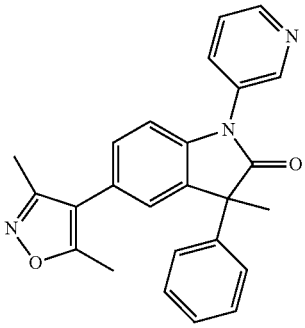 [SMILES: Cc1noc(C)c1-c1ccc2c(c1)C(C)(c1ccccc1)C(=O)N2c1cccnc1] |
| 21 | 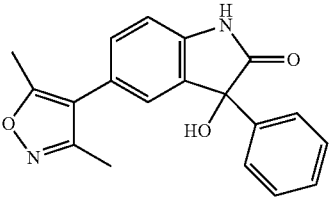 [SMILES: Cc1noc(C)c1-c1ccc2c(c1)C(O)(c1ccccc1)C(=O)N2] |
| 22 | 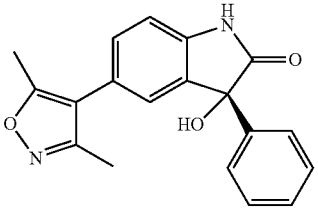 [SMILES: Cc1noc(C)c1-c1ccc2c(c1)[C@](O)(c1ccccc1)C(=O)N2] |
| 23 | 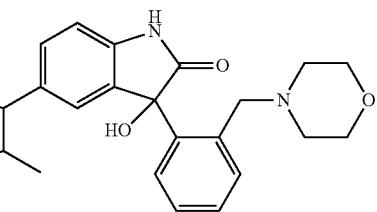 |
| 24 | 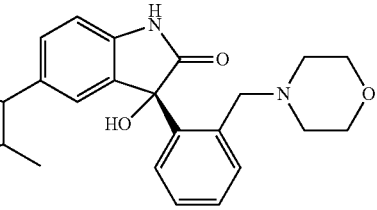 |
70
-continued
| EX# | Structure |
|---|---|
| 25 | 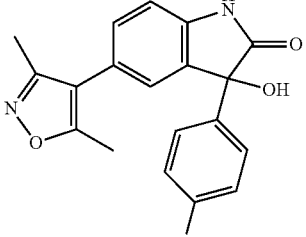 |
| 26 | 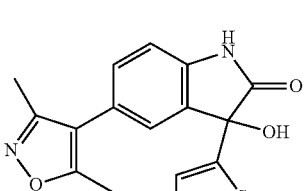 |
| 27 | 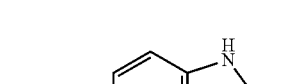 |
| 28 | 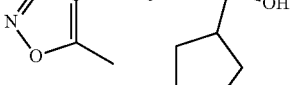 |
| 29 | 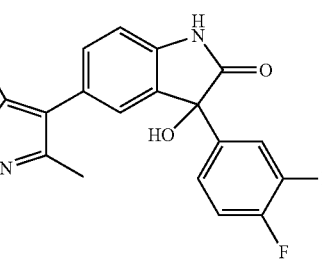 |
| 30 | 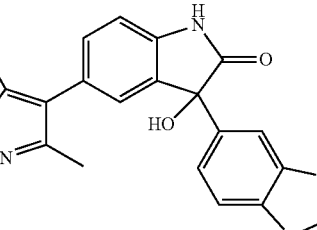 |

| EX# | Structure |
|---|---|
| 31 | (3,5-dimethylisoxazol-4-yl / 3-hydroxy-3-(pyridin-3-yl)indolin-2-one) |
| 32 | (3,5-dimethylisoxazol-4-yl / 3-hydroxy-3-(pyridin-2-yl)indolin-2-one) |
| 33 | (3,5-dimethylisoxazol-4-yl / 3-hydroxy-3-(o-tolyl)indolin-2-one) |
| 34 | (3,5-dimethylisoxazol-4-yl / 3-hydroxy-3-(tetrahydro-2H-pyran-4-yl)indolin-2-one) | and

| EX# | Structure |
|---|---|
| 35 | (3,5-dimethylisoxazol-4-yl / 3-hydroxy-3-(5-methylpyridin-3-yl)indolin-2-one) | or a pharmaceutically acceptable salt thereof.

14. A pharmaceutical composition comprising a therapeutically effective amount of a compound according to claim 1 optionally in combination with pharmaceutically acceptable excipients and/or carriers.

* * * * *